(12) United States Patent
McLennan

(10) Patent No.: US 10,948,139 B2
(45) Date of Patent: Mar. 16, 2021

(54) PORTABLE LIGHT HAVING A MOVABLE HEAD AND ASSEMBLY METHOD

(71) Applicant: STREAMLIGHT, INC., Eagleville, PA (US)

(72) Inventor: W. Ross McLennan, Perkasie, PA (US)

(73) Assignee: Streamlight, Inc., Eagleville, PA (US)

( * ) Notice: Subject to any disclaimer, the term of this patent is extended or adjusted under 35 U.S.C. 154(b) by 0 days.

(21) Appl. No.: 16/738,282

(22) Filed: Jan. 9, 2020

(65) Prior Publication Data

US 2020/0224836 A1 Jul. 16, 2020

Related U.S. Application Data

(63) Continuation of application No. 29/716,897, filed on Dec. 12, 2019, and a continuation of application No. 29/676,840, filed on Jan. 15, 2019.

(Continued)

(51) Int. Cl.
*F21L 4/04* (2006.01)
*F21V 21/08* (2006.01)
(Continued)

(52) U.S. Cl.
CPC ............. *F21L 4/04* (2013.01); *F21V 9/083* (2013.01); *F21V 14/065* (2013.01);
(Continued)

(58) Field of Classification Search
CPC ......... F21L 4/04; F21L 4/045; F21V 23/0428; F21V 14/065; F21V 14/085
See application file for complete search history.

(56) References Cited

U.S. PATENT DOCUMENTS

| D221,895 S | 9/1971 | Angibaud |
| 4,228,485 A | 10/1980 | Hubbard et al. |

(Continued)

FOREIGN PATENT DOCUMENTS

| EM | 004752129-0001 | 3/2018 |
| EM | 006620779-0001 | 7/2019 |

OTHER PUBLICATIONS

SureFire U2 Ultra LED Flashlight (including larger image), © 2001-2005, http://www.surefire.com/maxexp/main/co_disp/displ/prrfnbr/24187/sesent/00, Printed Dec. 1, 2005, 3 pages.

(Continued)

*Primary Examiner* — Alexander K Garlen
(74) *Attorney, Agent, or Firm* — Clement A. Berard, Esq.; Dann, Dorfman, Herrell & Skillman, PC

(57) ABSTRACT

A portable light and assembly method may comprise: a light body supporting a source of electrical power and a light head having a light source that produces light. A rotating joint may include: a hollow cylindrical central member extending from one of the light body and the light head in a cylindrical bore of complementary size and shape in the other of the light body and the light head, a fastener retaining the hollow cylindrical member in the cylindrical bore, and one or more electrical conductors extending through the hollow cylindrical member of the rotating joint to connect the source of electrical power to the light source. A hinged cover has a latch including an arm member engaging a feature of the light body or including a thumb screw engaging a threaded hole of the light body, to retain the closed cover against the light body.

44 Claims, 20 Drawing Sheets

Related U.S. Application Data

(60) Provisional application No. 62/793,681, filed on Jan. 17, 2019.

(51) Int. Cl.
*F21V 21/088* (2006.01)
*F21V 23/04* (2006.01)
*F21V 9/08* (2018.01)
*F21V 14/06* (2006.01)

(52) U.S. Cl.
CPC ...... *F21V 21/0832* (2013.01); *F21V 21/0885* (2013.01); *F21V 23/0414* (2013.01); *F21V 23/0492* (2013.01)

(56) References Cited

U.S. PATENT DOCUMENTS

| | | |
|---|---|---|
| 4,346,329 A | 8/1982 | Schmidt |
| 4,649,323 A | 3/1987 | Pearlman et al. |
| D296,827 S | 7/1988 | Yuen |
| D328,144 S | 7/1992 | Yuen |
| 5,133,329 A | 7/1992 | Rodseth et al. |
| 5,158,357 A | 10/1992 | McDermott |
| 5,191,209 A | 3/1993 | Rodseth et al. |
| D335,715 S | 5/1993 | Wan |
| 5,248,919 A | 9/1993 | Hanna et al. |
| D349,776 S | 8/1994 | Yuen |
| 5,359,779 A | 11/1994 | Polk |
| D355,358 S | 2/1995 | Starr et al. |
| 5,418,433 A | 5/1995 | Nilssen |
| D367,087 S | 2/1996 | Mathews |
| D368,145 S | 3/1996 | Smith |
| D378,434 S | 3/1997 | Petterson |
| 5,629,105 A | 5/1997 | Matthews |
| 5,682,558 A | 10/1997 | Kirigaya et al. |
| 5,871,272 A | 2/1999 | Sharrah et al. |
| D407,514 S | 3/1999 | Yuen |
| D410,557 S | 6/1999 | Petterson |
| D413,993 S | 9/1999 | Yuen |
| 5,988,828 A * | 11/1999 | Prince ...................... F21L 4/04 362/191 |
| 6,012,824 A | 1/2000 | Sharrah et al. |
| 6,024,471 A | 2/2000 | McDermott |
| 6,046,572 A | 4/2000 | Matthews |
| D425,642 S | 5/2000 | Zeller |
| 6,079,853 A | 6/2000 | Evans |
| 6,140,776 A | 10/2000 | Rachwal |
| 6,184,930 B1 | 2/2001 | Mitsuhashi et al. |
| 6,222,138 B1 | 4/2001 | Matthews et al. |
| 6,239,555 B1 | 5/2001 | Rachwal |
| 6,249,089 B1 | 6/2001 | Bruwer |
| 6,250,771 B1 | 6/2001 | Sharrah et al. |
| 6,296,367 B1 | 10/2001 | Parsons et al. |
| 6,307,328 B1 | 10/2001 | Ko et al. |
| 6,388,390 B2 | 5/2002 | Rachwal |
| 6,443,605 B1 | 9/2002 | Kasboske |
| D467,375 S | 12/2002 | Lynch et al. |
| 6,523,972 B2 | 2/2003 | Sharrah et al. |
| 6,621,225 B2 | 9/2003 | Bruwer |
| 6,650,066 B2 | 11/2003 | Bruwer |
| 6,659,621 B2 | 12/2003 | Sharrah et al. |
| D487,810 S | 3/2004 | Kingston et al. |
| 6,817,730 B2 | 11/2004 | Sharrah et al. |
| 6,841,941 B2 | 1/2005 | Kim et al. |
| D505,739 S | 5/2005 | Hajianpour |
| 6,913,371 B2 | 7/2005 | Ping |
| 6,952,084 B2 | 10/2005 | Bruwer |
| D512,791 S | 12/2005 | Ping |
| 6,984,900 B1 | 1/2006 | Bruwer |
| D518,213 S | 3/2006 | Ping |
| D536,464 S | 2/2007 | Kingston |
| 7,229,189 B2 | 6/2007 | Parker |
| D548,863 S | 8/2007 | Shiu |
| D549,379 S * | 8/2007 | Sharrah ........................ D26/60 |
| D560,297 S | 1/2008 | Brown et al. |
| 7,344,270 B2 | 3/2008 | Kim |
| D567,418 S | 4/2008 | Gilbert |
| D590,971 S | 4/2009 | Spartano et al. |
| 7,549,766 B2 | 6/2009 | Sharrah et al. |
| D599,925 S | 9/2009 | Kingston |
| D605,795 S | 12/2009 | Baker |
| D611,629 S | 3/2010 | Sharrah et al. |
| 7,731,385 B2 | 6/2010 | Spartano |
| D620,161 S | 7/2010 | Kang |
| D681,246 S | 4/2013 | Keeley |
| D681,858 S | 5/2013 | Sharrah |
| 8,727,561 B2 | 5/2014 | Sharrah et al. |
| 8,764,217 B2 | 7/2014 | Hao |
| 8,779,683 B2 | 7/2014 | Snyder |
| D713,077 S | 9/2014 | Hao |
| 8,833,962 B2 | 9/2014 | Ko |
| 8,905,573 B2 | 12/2014 | Sharrah |
| D728,139 S | 4/2015 | Wang |
| D767,184 S | 9/2016 | Fitch et al. |
| 9,739,467 B1 | 8/2017 | Lehman |
| D824,063 S | 7/2018 | Hutchens |
| 10,030,847 B2 | 7/2018 | Worman et al. |
| D829,354 S | 9/2018 | Cacciabeve |
| D833,661 S | 11/2018 | Ma |
| 10,119,663 B2 | 11/2018 | Bayat |
| D837,428 S | 1/2019 | Arena |
| 10,378,744 B2 | 8/2019 | Arena |
| 10,400,962 B2 | 9/2019 | Keller |
| D866,030 S | 11/2019 | Bao |
| D884,942 S | 5/2020 | Sharrah |
| 2002/0021573 A1 | 2/2002 | Zhang |
| 2002/0097576 A1 | 7/2002 | Sharrah et al. |
| 2003/0151914 A1 | 8/2003 | Kish |
| 2004/0217655 A1 | 11/2004 | Bruwer |
| 2004/0227409 A1 | 11/2004 | Bruwer |
| 2005/0077837 A1 | 4/2005 | Kim et al. |
| 2005/0083626 A1 | 4/2005 | Bruwer |
| 2005/0121980 A1 | 6/2005 | Bruwer |
| 2005/0122710 A1 | 6/2005 | Kim |
| 2005/0122712 A1 | 6/2005 | Kim |
| 2005/0122714 A1 | 6/2005 | Matthews et al. |
| 2005/0128741 A1 | 6/2005 | Matthews et al. |
| 2005/0140310 A1 | 6/2005 | Bruwer |
| 2005/0237737 A1 | 10/2005 | Kim |
| 2006/0044792 A1 | 3/2006 | Dallas |
| 2008/0049418 A1 * | 2/2008 | Ross ................... F21V 33/0076 362/109 |
| 2008/0049433 A1 * | 2/2008 | Sharrah ................ H03K 17/968 362/362 |
| 2010/0046211 A1 * | 2/2010 | Spartano ................. F21V 15/01 362/157 |
| 2012/0033415 A1 * | 2/2012 | Sharrah ................... F21V 21/08 362/199 |
| 2012/0182723 A1 | 7/2012 | Sharrah |
| 2016/0018071 A1 | 1/2016 | Sharrah |
| 2016/0018090 A1 | 1/2016 | Sharrah |
| 2017/0284646 A1 * | 10/2017 | Arena ................. F21V 23/0414 |
| 2020/0224836 A1 | 7/2020 | McLennan |

OTHER PUBLICATIONS

LED Lights Comparison Chart, http://www.surefire.com/surefire/content/comparechart_LED.html, Printed Dec. 5, 2005, 1 page.

Flashlight Reviews and LED Modifications, FlashlightReviews.com, "In2theLight Trio, 29 LED Flashlight", prior to Sep. 18, 2017 filing date, 7 pages.

Hama, "Walk Light LED photos", prior to Sep. 18, 2017 filing date, 5 pages.

Streamlight. "Sidewinder® Angle Head Flashlight w/C4® LED Product Fact Sheet", Mar. 31, 2008, 2pgs.

Streamlight. "Sidewinder® LED Hands Free Light", prior to Sep. 18, 2017 filing date, 2 pages https://www.streamlight.com/products/detail/index/sidewinder.

Streamlight, Inc., "Portable Light Having a Movable Head", Design U.S. Appl. No. 29/676,840, filed Jan. 15, 2019, 30 pages.

Streamlight, Inc., "Portable Light Having a Movable Head", Design U.S. Appl. No. 29/716,897, filed Dec. 12, 2019, 30 pages.

(56) References Cited

OTHER PUBLICATIONS www.jobrien.com: Nebo Cryket 6437 Work Light/Spot Light (250 Lumen). Undated online product page. Retrieved on Sep. 2, 2020, from <https://www.jobrien.com/nebo-cryket-6437-work-light-spot-light?utm_campaign=SC+Shopping+-+General . . . > (Year: 2020).
www.amazon.com: New Work Flashlight, Magnetic Base Work 10W Flashlight Rechargeable, Handheld Flashlights 360° Rotate,. Date uploaded Dec. 15, 2019 [site visited Sep. 2, 2020]. Retrieved from internet, <https://www.amazon.com/Flashlight-Rechargeable-Flashlights-Inspection-Household/ . . . > (Year: 2019).
United States Patent and Trademark Office, "Notice of Allowance and Fees Due", Design U.S. Appl. No. 29/676,840, dated Oct. 28, 2020.

* cited by examiner

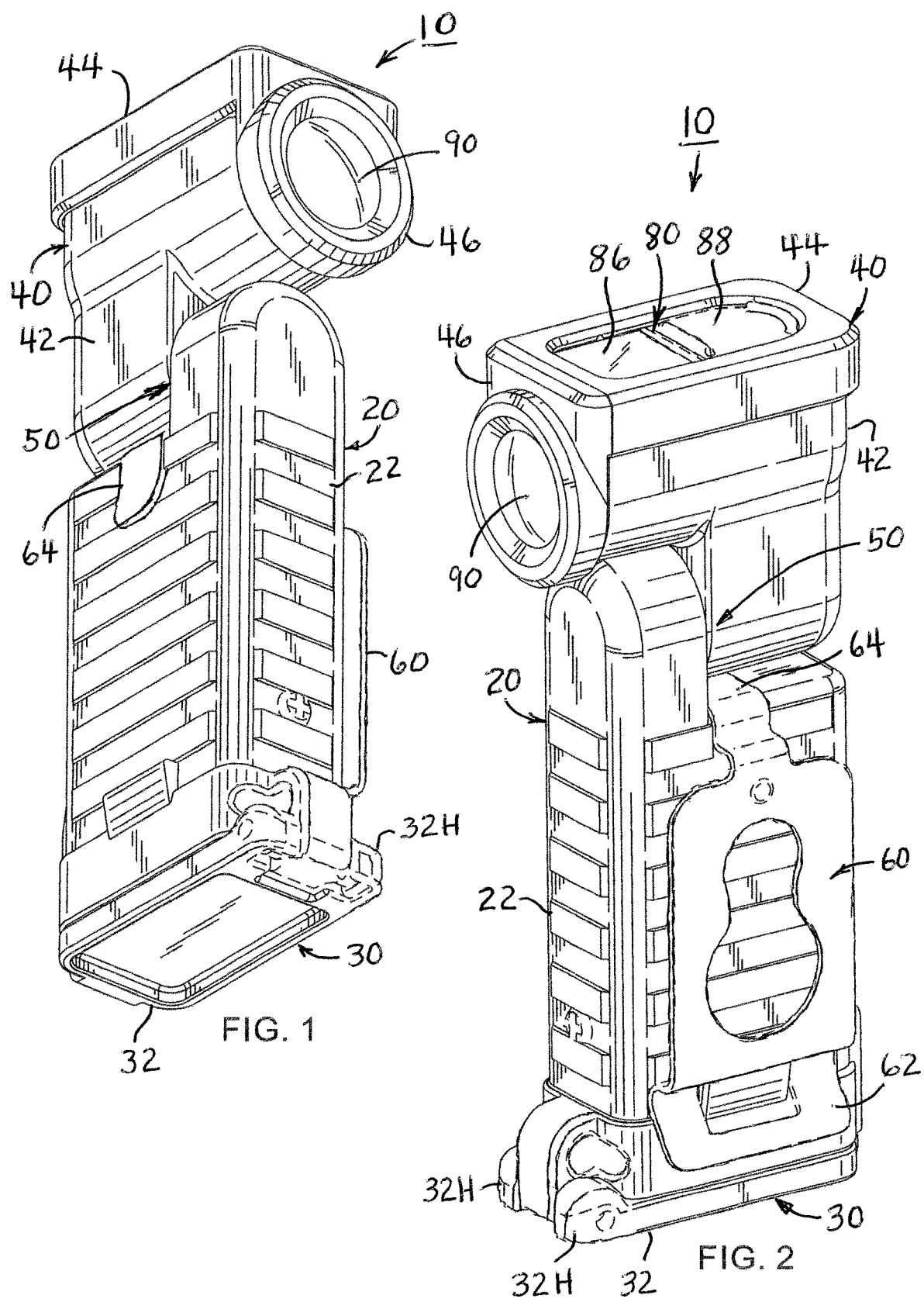

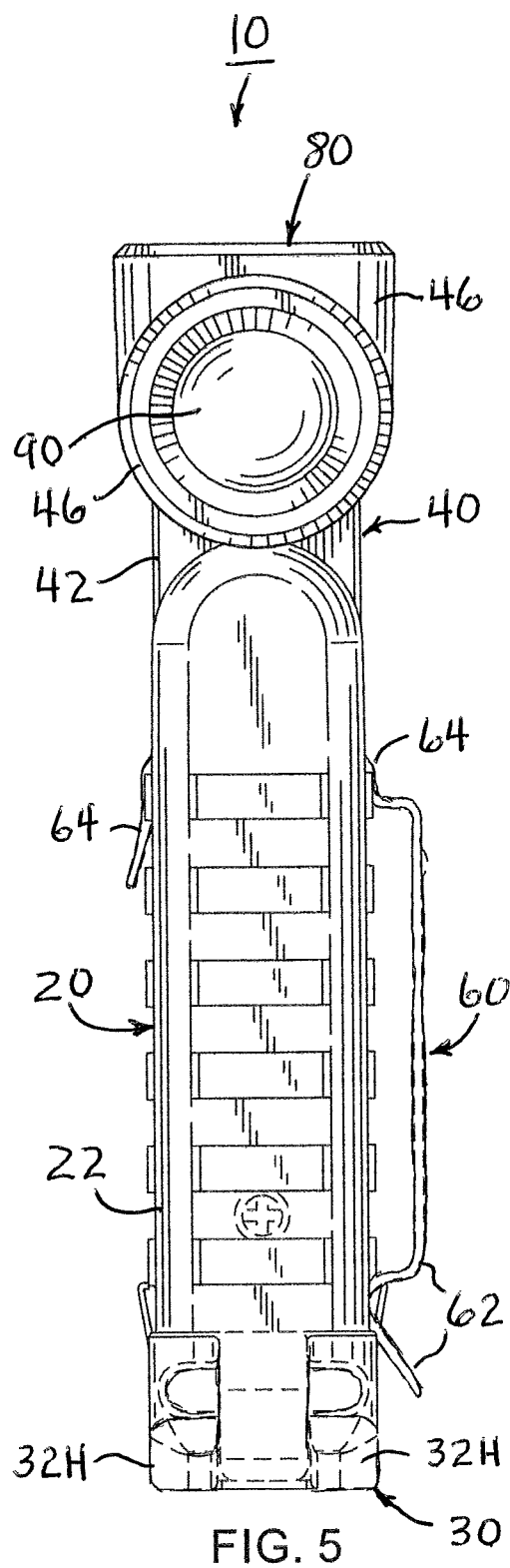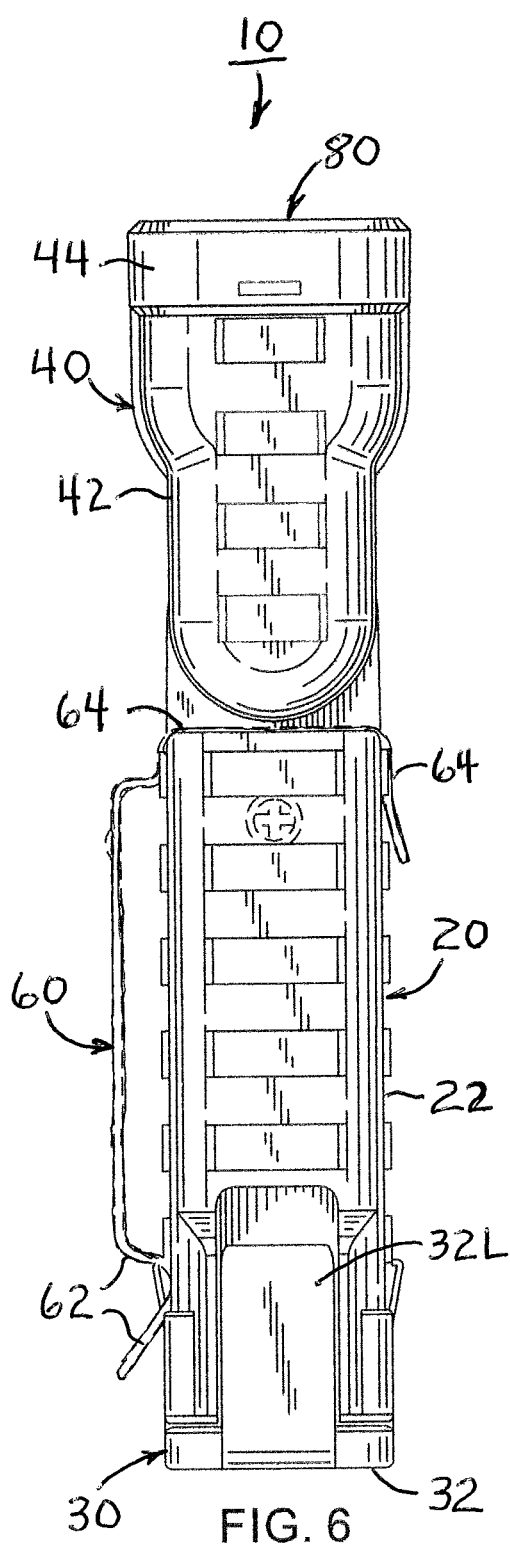

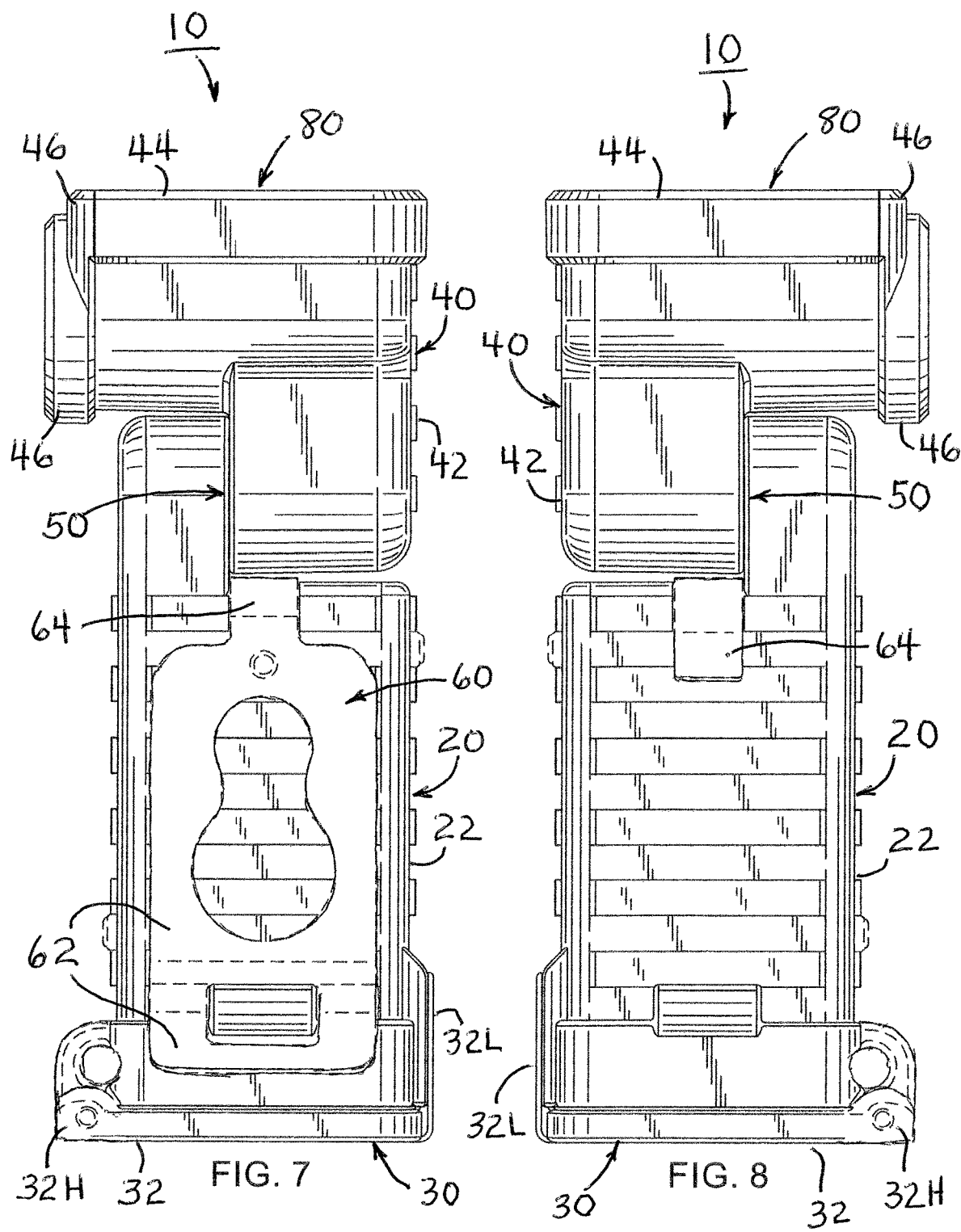

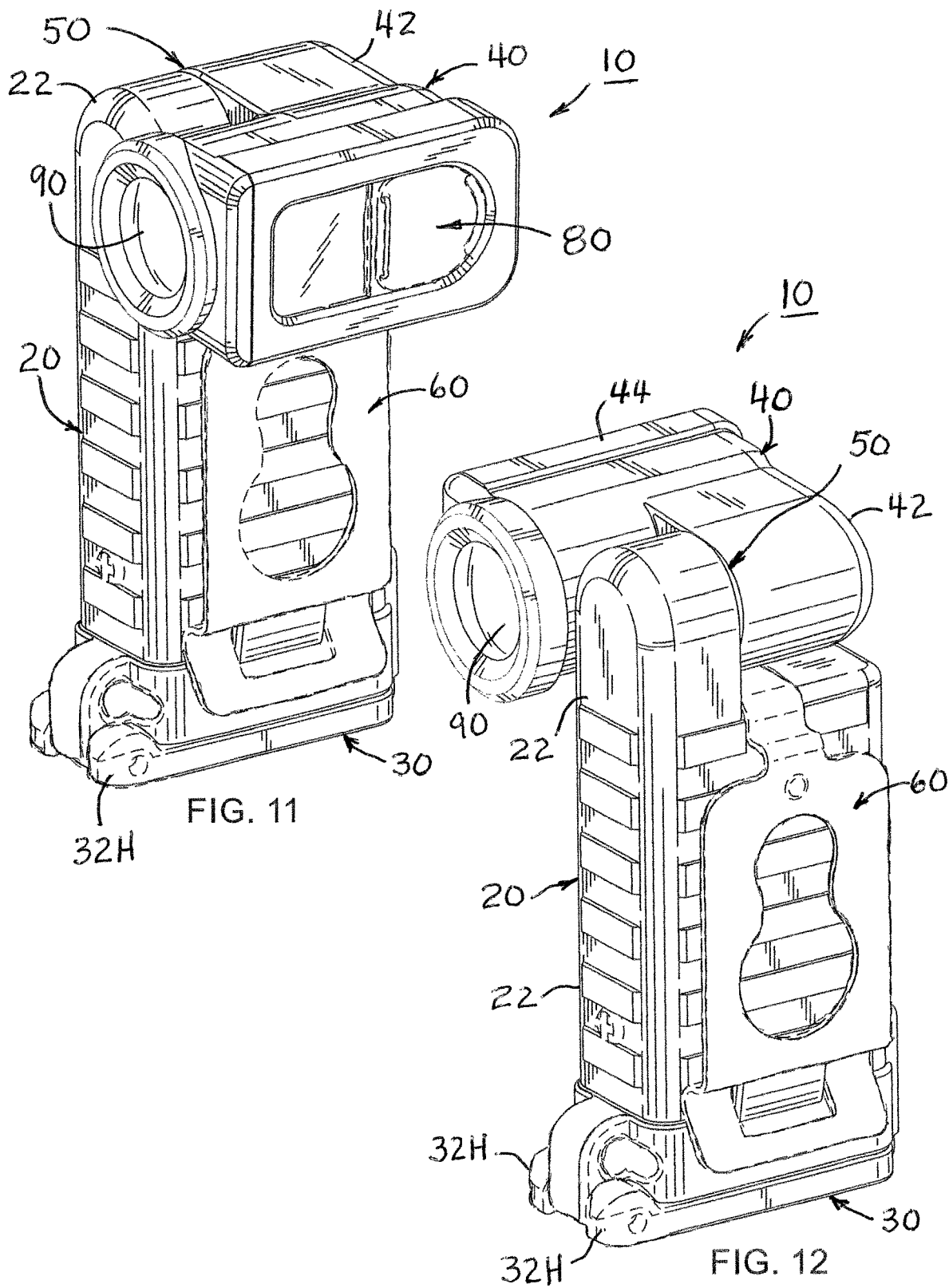

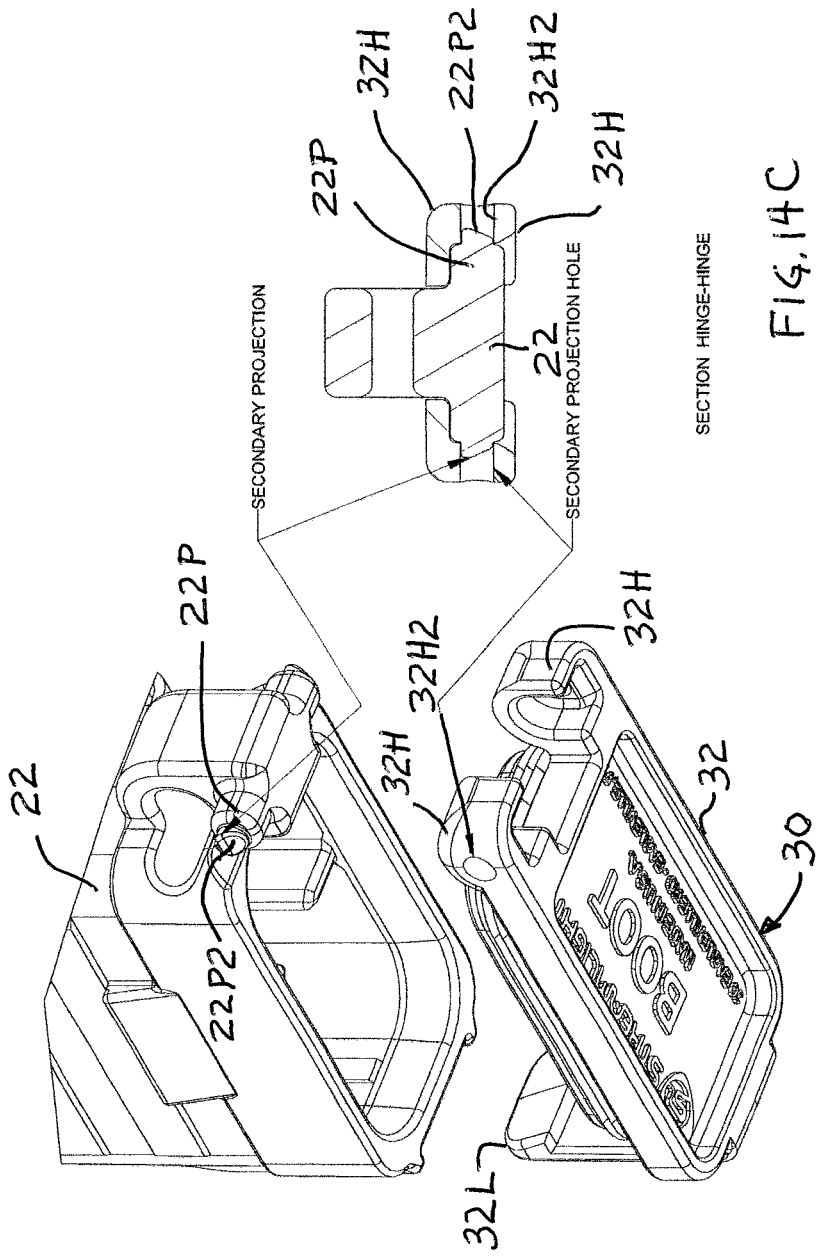

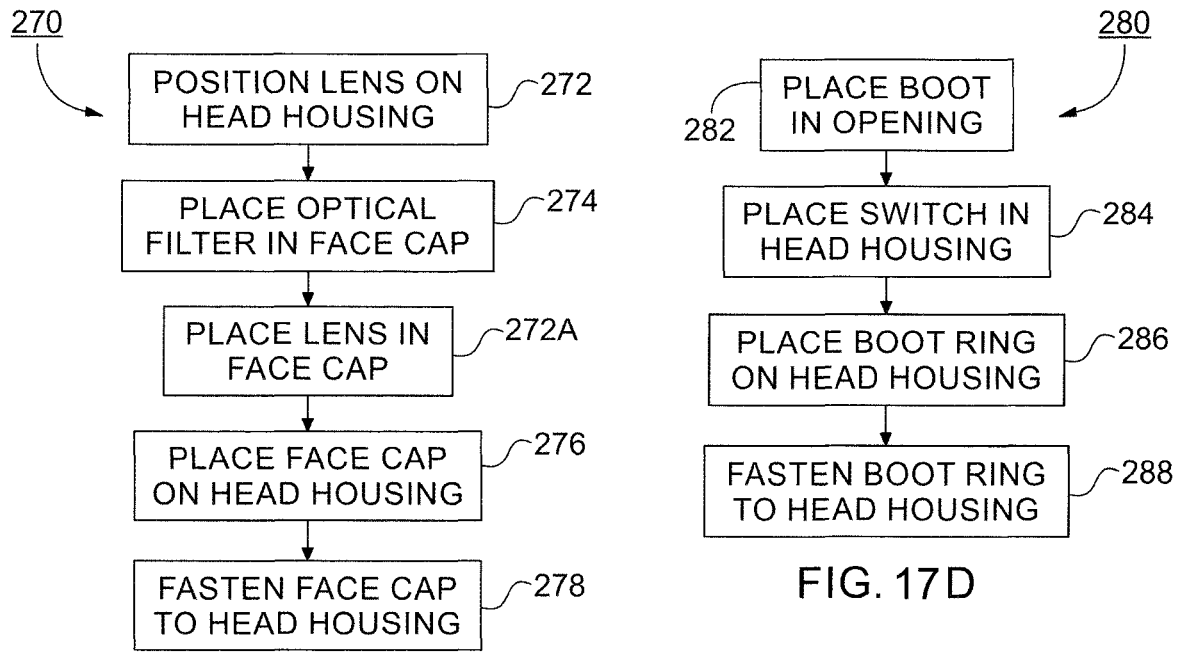
FIG. 17C
FIG. 17D
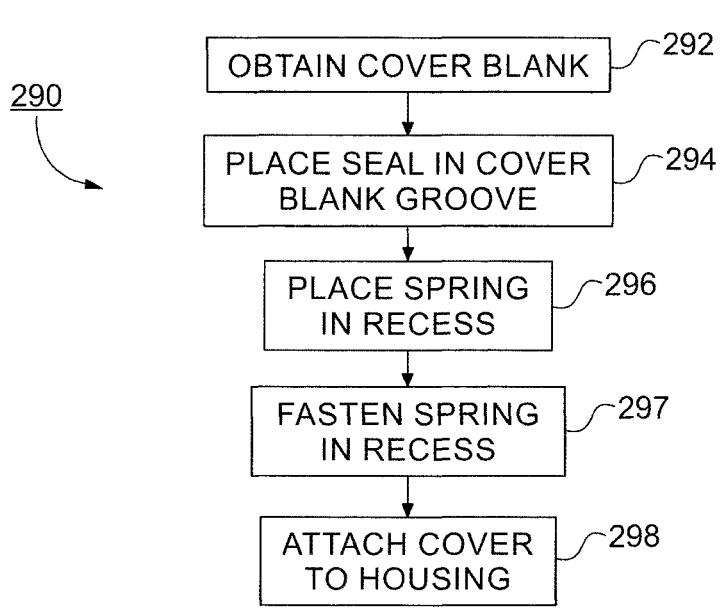
FIG. 17E

PORTABLE LIGHT HAVING A MOVABLE HEAD AND ASSEMBLY METHOD

This Application claims the benefit and priority of, and is a continuation of:

U.S. patent application Ser. No. 29/716,897 filed Dec. 12, 2019, entitled "PORTABLE LIGHT HAVING A MOVABLE HEAD," and of U.S. Patent Application No. 62/793,681 filed Jan. 17, 2019, entitled "PORTABLE LIGHT HAVING A MOVABLE HEAD AND ASSEMBLY METHOD," and of U.S. patent application Ser. No. 29/676,840 filed Jan. 15, 2019, entitled "PORTABLE LIGHT HAVING A MOVABLE HEAD,"

each of which is hereby incorporated herein by reference in its entirety.

The present invention relates to a portable light having a movable head and an assembly method therefor.

Portable lights having a movable head typically have a light body which supports inter alia a power source and a light head which supports inter alia a light source. These kind of lights require a rotating joint between the light body and the light head so that the light head is movable, e.g., can pivot or swivel, relative to the light body.

Various arrangements for such rotating joints have been proposed and used, and many, if not most, have significant complexity that can, e.g., reduce the reliability and service life of the joint, and therefore, of the light. In addition, because of the complexity of the rotating joint, assembly of that joint is likewise complex and, because of the small spaces within a typical light and the many different parts that need to be put and secured into their respective places, intricate and time consuming. A joint having many parts and complex assembly tends to increase the cost for parts and for assembling a light.

Applicant believes there may be a need for a portable light having a movable light head that is configured to reduce complexity of the light, e.g., of the rotating joint and other elements thereof, and desirably also improve durability and reduce manufacturing time.

Applicant believes there may be a need for a portable light having a cover providing access for installing and removing an electrical power source, e.g., a battery cover, that can be easily assembled and installed on the portable light, and also desirably to reduce complexity and manufacturing time.

Applicant also believes there may be a need for a method for assembling a portable light having a movable light head that is relatively straightforward and takes advantage of the reduced complexity of the light, e.g., of the rotating joint and other elements thereof.

Accordingly, a portable light may comprise: a light body for supporting a source of electrical power and a light head for supporting a light source; a rotating joint including: a hollow cylindrical member extending from one of the light body and the light head and a bore complementary in size and shape to the hollow cylindrical member in the other of the light body and the light head; and a fastener engaging the hollow cylindrical member to retain the hollow cylindrical member in the bore; and one or more electrical conductors extending through the hollow cylindrical member to connect the source of electrical power and the light source; and an electrical switch coupled in circuit with the light source and the source of electrical power via the one or more electrical conductors for selectively energizing the light source to produce light.

The portable light may also comprise: a light body for supporting a source of electrical power and a light head for supporting a light source; that produces light when energized by the source of electrical power; a rotating joint joining the light body and the light head in movable relationship and defining an opening therebetween; one or more electrical conductors extending through the opening to connect the source of electrical power to the light source; wherein the light body has an opening and at least one projection proximate the opening, a cover of a size and shape for covering the opening and having at least one hook member for engaging the at least one projection thereby defining a hinge and having a latch projection for retaining the cover against the light body; and an electrical switch coupled in circuit with the light source and the source of electrical power via the one or more electrical conductors for selectively energizing the light source.

Additionally, a method for assembling a portable light may comprise:

obtaining a light body housing either having a hollow cylindrical member extending therefrom or a cylindrical bore complementary in size and shape to the hollow cylindrical member;

obtaining a light head housing having the other of the hollow cylindrical member extending therefrom or the cylindrical bore therein;

inserting the hollow cylindrical member into the cylindrical bore;

fastening the hollow cylindrical member in the cylindrical bore to form a rotating joint joining the light body housing and the light head housing in movable relationship;

obtaining a battery contact assembly having at least two electrical conductors extending therefrom;

placing the battery contact assembly into the light body housing and the at least two electrical conductors through the hollow cylindrical central member;

connecting the at least two electrical conductors to a light source; and placing the light source into the light head housing.

In summarizing the arrangements described and/or claimed herein, a selection of concepts and/or elements and/or steps that are described in the detailed description herein may be made or simplified. Any summary is not intended to identify key features, elements and/or steps, or essential features, elements and/or steps, relating to the claimed subject matter, and so is not intended to be limiting and should not be construed to be limiting of or defining of the scope and breadth of the claimed subject matter.

BRIEF DESCRIPTION OF THE DRAWING

The detailed description of the preferred embodiment(s) will be more easily and better understood when read in conjunction with the FIGURES of the Drawing which include:

FIGS. 1, 2, 3 and 4 are perspective views of an example embodiment of a portable light having a movable head when viewed from different directions.

FIGS. 5, 6, 7, 8, 9 and 10 are six orthogonal views of the four sides and of the upper and lower ends of the example light;

FIGS. 11 and 12 are perspective views of the example portable light having a movable head illustrating alternative positions of the movable head thereof;

FIGS. 17A through 17E are flow diagrams illustrating various aspects of the process.

Figure 3:
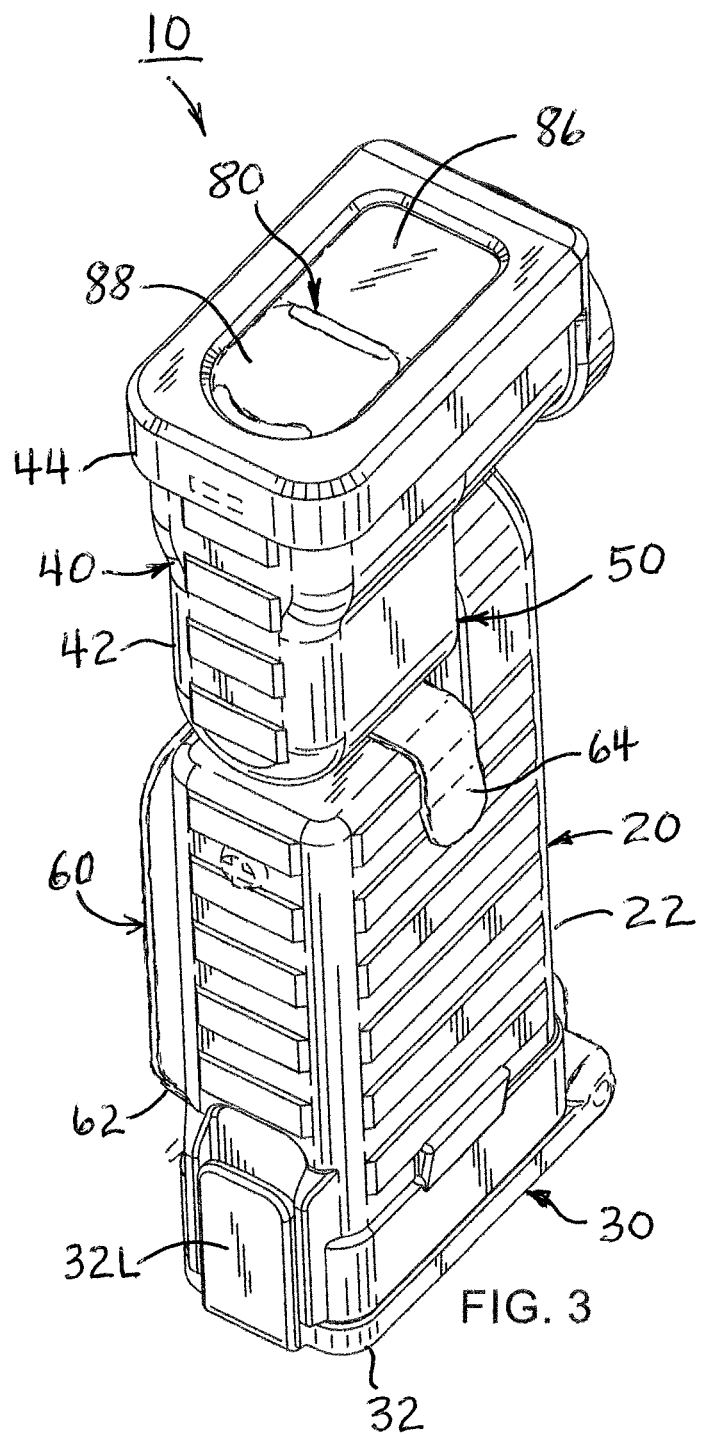

In the Drawing, where an element or feature is shown in more than one drawing figure, the same alphanumeric designation may be used to designate such element or feature in each figure, and where a closely related or modified element is shown in a figure, the same alphanumerical designation may be primed or designated "a" or "b" or the like to designate the modified element or feature. Similar elements or features may be designated by like alphanumeric designations in different figures of the Drawing and with similar nomenclature in the specification. As is common, the various features of the drawing are not to scale, the dimensions of the various features may be arbitrarily expanded or reduced for clarity, and any value stated in any Figure is by way of example only.

DESCRIPTION OF THE PREFERRED EMBODIMENT(S)

Figure 3A:
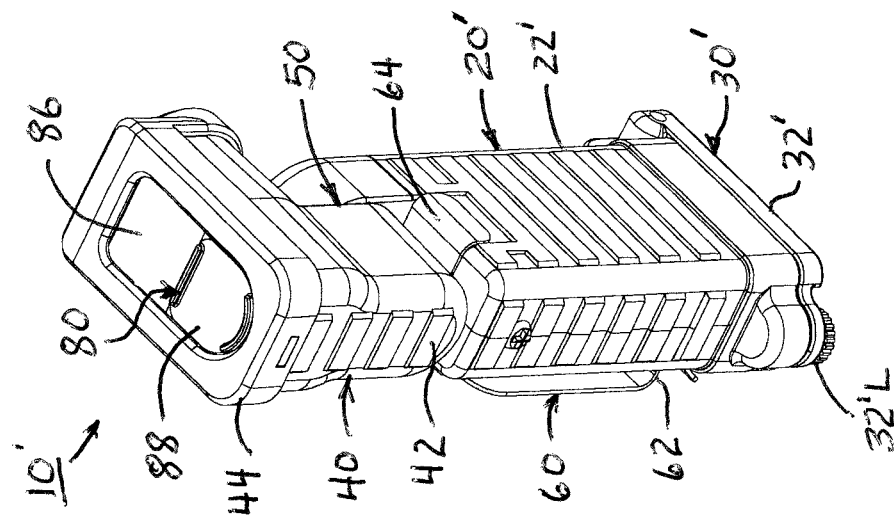
FIGS. 3A and 4A are perspective views of another example embodiment of a portable light having a movable head when viewed from different directions.
Figure 4A:
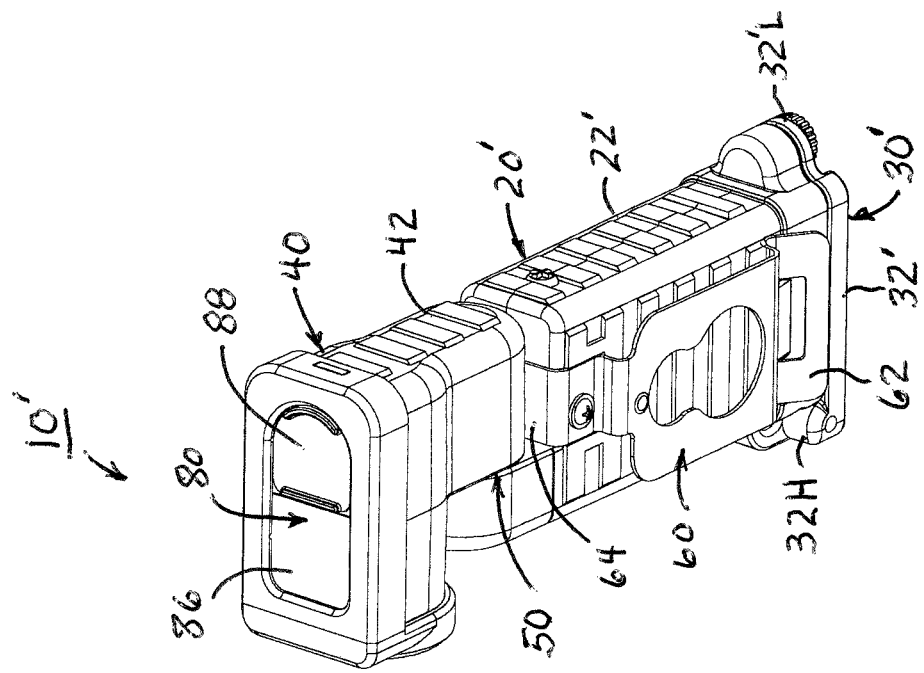
Figure 4:
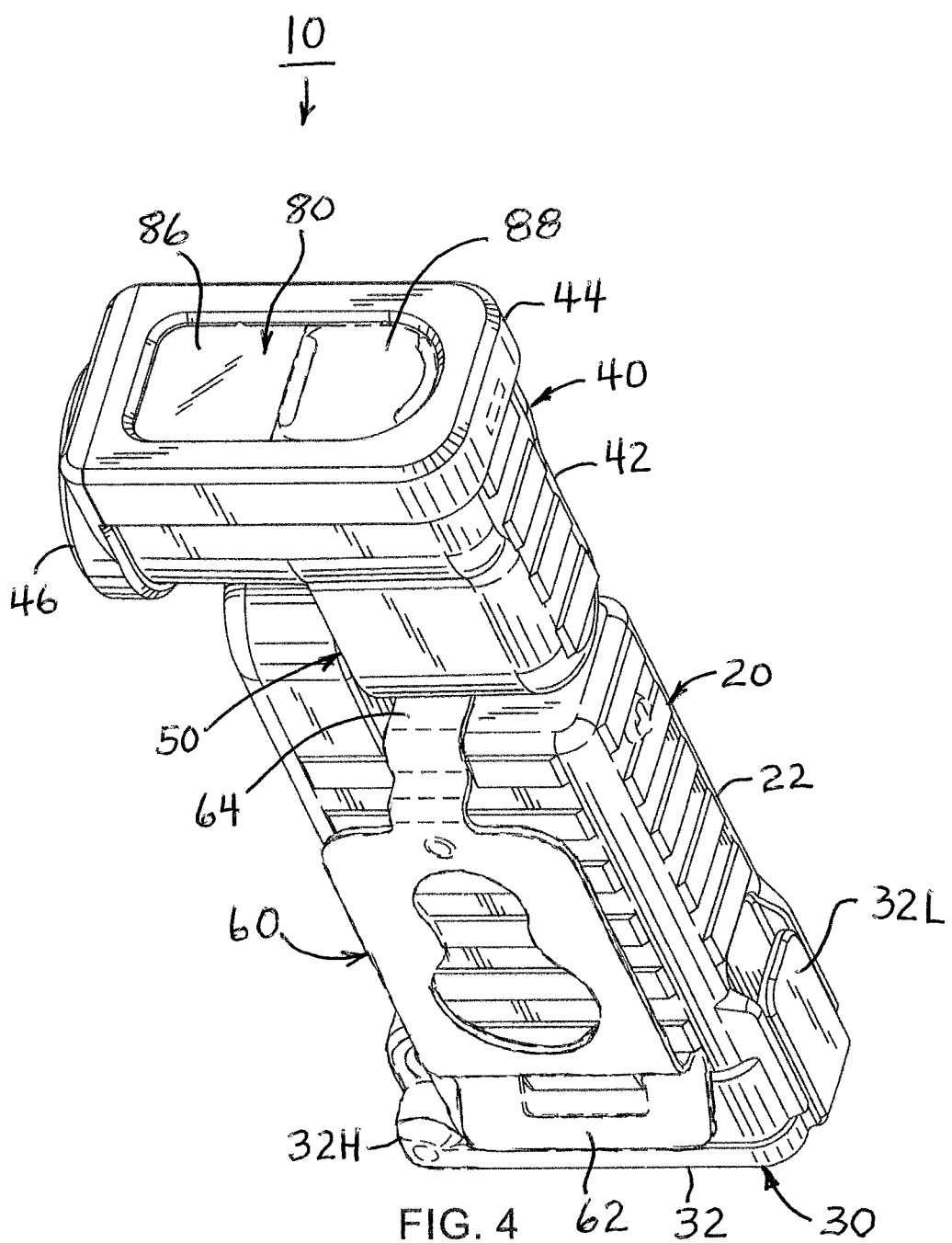
Figure 9:
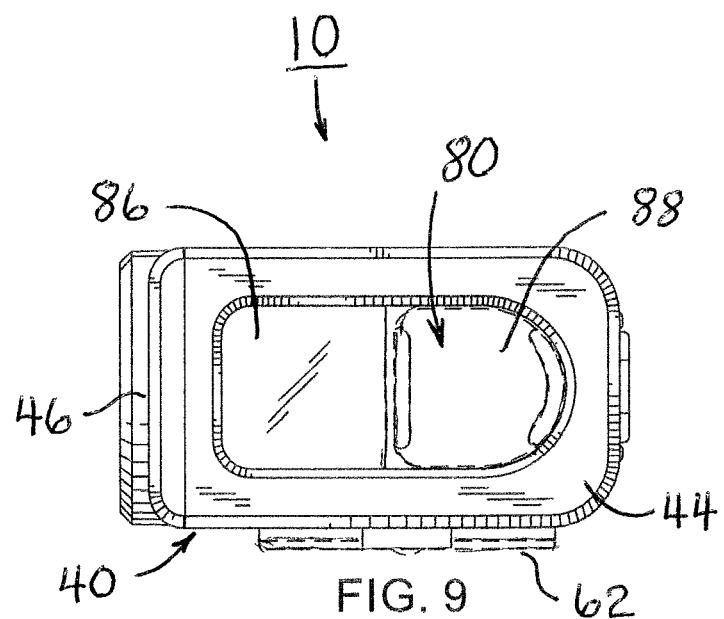
Figure 10:
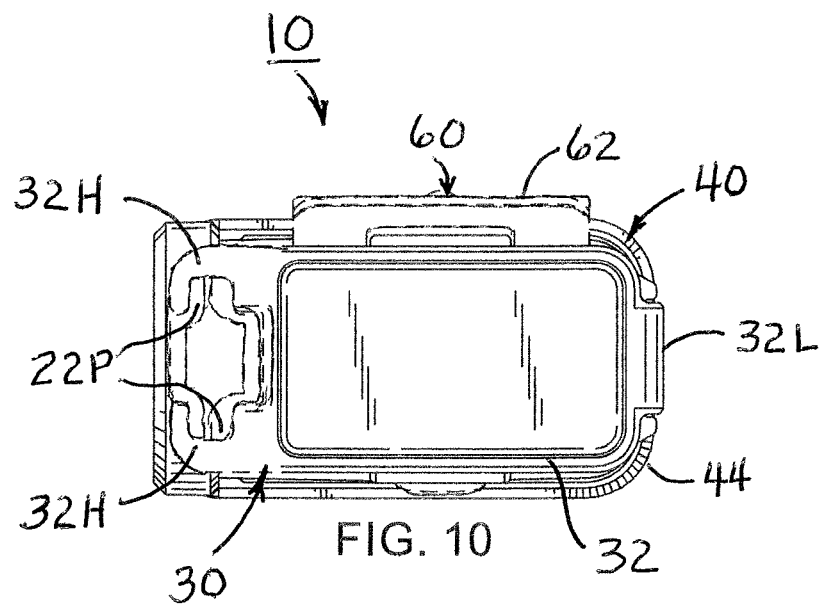
Figures 13A, 13B:
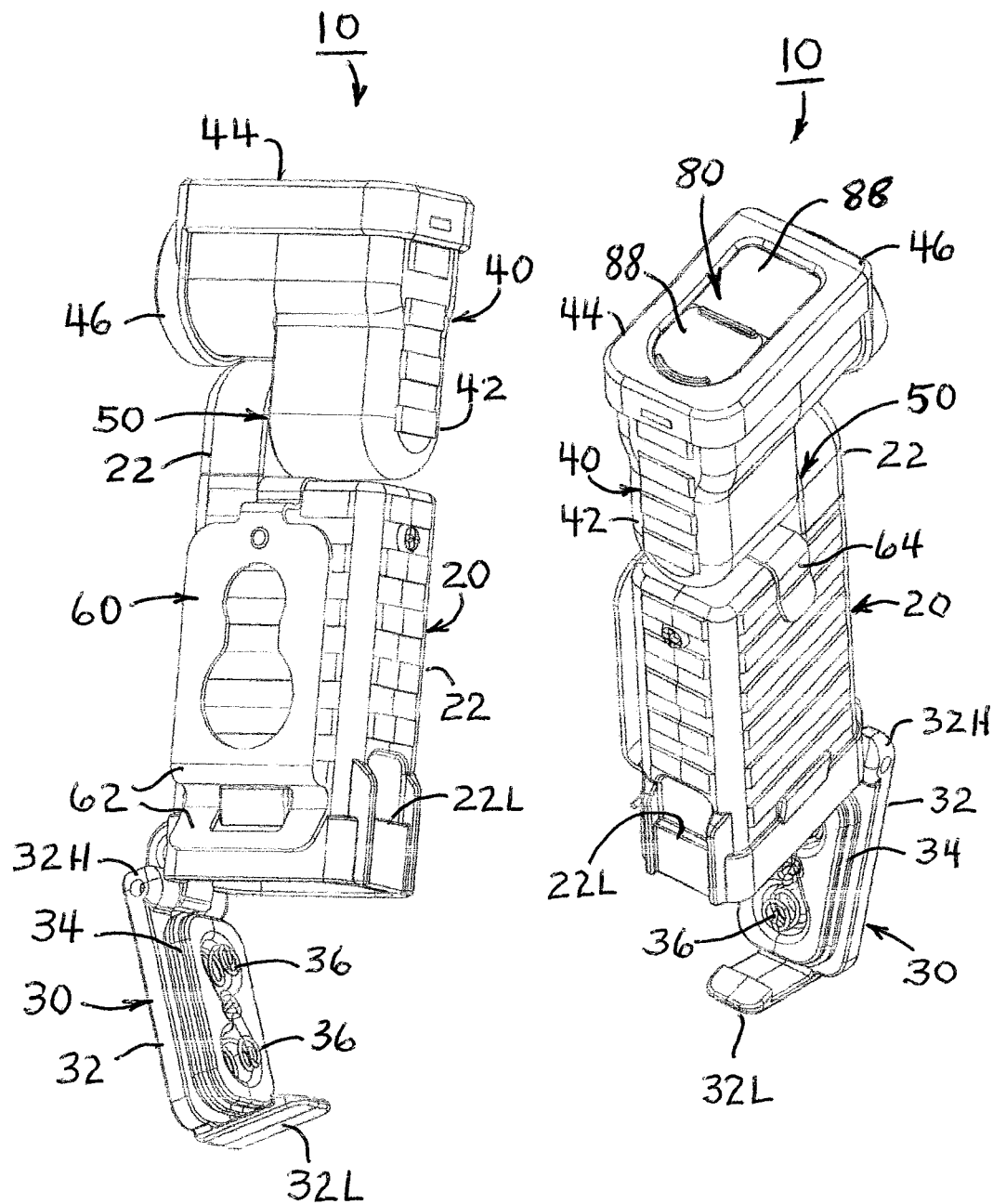
FIGS. 13A and 13B are perspective views of the example light of FIGS. 1-12, and FIGS. 13C and 13D are perspective views of the example light of FIGS. 3A and 4A, each with a respective example cover thereof in an open position.
Figures 13C, 13D:
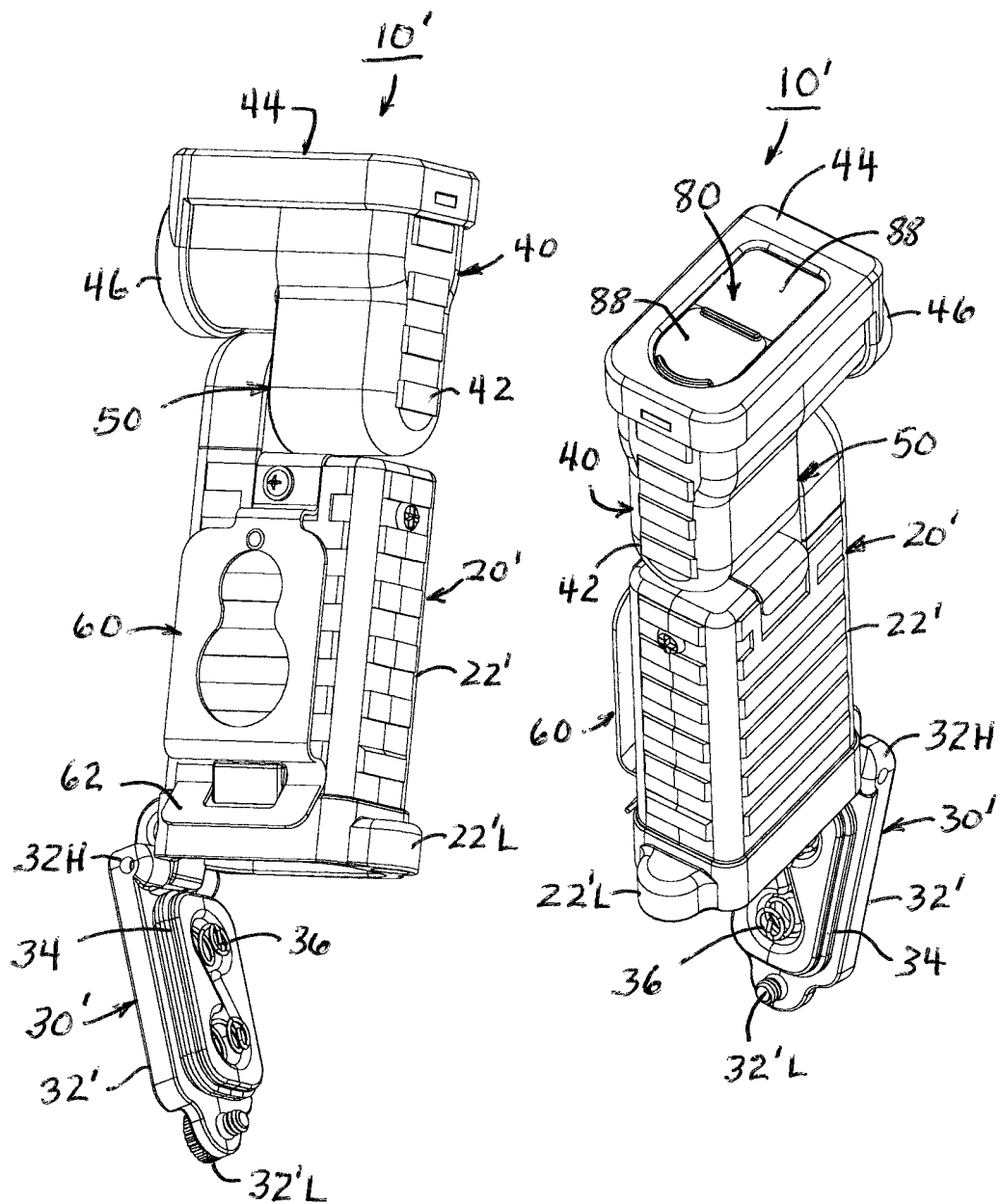

FIGS. 1, 2, 3 and 4 are perspective views of an example embodiment of a portable light 10 having a movable head 40 when viewed from different directions, and FIGS. 3A and 4A are perspective views of another example embodiment of a portable light 10' having a movable head 40 when viewed from different directions; FIGS. 5, 6, 7, 8, 9 and 10 are six orthogonal views of the four sides and of the upper and lower ends of the example light 10 of FIGS. 1-4; FIGS. 11 and 12 are perspective views of the example portable light 10 having a movable head 40 illustrating alternative positions of the movable head 40 thereof; and FIGS. 13A and 13B are perspective views of the example light of FIGS. 1-12, and FIGS. 13C and 13D are perspective views of the example light of FIGS. 3A and 4A, each with a respective example cover thereof in an open position. Portable lights 10, 10' have a light body 20, 20'; that is connected via a pivoting joint 50 to a movable head 40, e.g., light head 40, which contains a light source 80. Portable lights 10 and 10' are the same except for the arrangement of battery cover 30, 30' and the latch 32L, 32'L thereof for retaining cover 30, 30' in a closed position.

Light body 20 includes a light body housing 22 that has an internal cavity for receiving a source of electrical power, e.g., one or more batteries, therein. The opening of housing 22 through which the one or more batteries are installed and removed is covered by a latching cover assembly 30. Light head 40, which is movable, e.g., pivotable, relative to light body 20 via pivoting joint 50 which connects light body 20 and light head 40, includes a light head housing 42 which includes a light source 80 interior thereto. Light body 20' and housing 22' are the same as light body 20 and housing 22 except for the arrangement of the latch 32L, 32'L as described herein.

Light is emitted from light 10 by a light source 80 of light head 40 that is selectively energized by actuating an actuator 90 on the exterior of light head 40 to operate an electrical switch internal thereto. Light source 80 emits light through lens 86, e.g., a transparent plastic lens 86, that covers a light emitting device, e.g., a light emitting diode (LED), internal to light head 40. A slidable optical filter 88 is provided in face cap 44, or bezel 44, that can be moved in front of the light emitting device to optically change a characteristic of the emitted thereby. Optical filter 88 may be a colored filter, e.g., a red or green filter 88, or a diffusing filter 88, e.g., a translucent diffuser 88, as may be desired.

Light body 20, 20' includes a light body housing 22, 22' having an interior cavity for receiving a source of electrical power, e.g., a battery, fuel cell and the like. Access to the interior cavity is via an opening in, e.g., the bottom end of housing 22, that is covered by a cover assembly 30, 30'. Cover assembly 30, 30' includes a cover 32, 32' that has one or more hooks 32H at one end thereof that engage one or more projections of body housing 22, thereby providing a hinge at the one end of the cover 32. Cover 32, 32' has a latch 32L, 32'L at an end opposite to hooks 32H thereof that engages a complementary latching feature of body housing 22, 22'.

Cover assembly 30, 30' includes a cover 32, 32', e.g., a molded plastic cover 32, 32' that has one of more hooks 32H and a latching member 32L, 32'L at opposing ends thereof so that cover assembly 30, 30' is hinged on light body housing 22, 22' and will releasably latch to light body 20, 20' when cover assembly 30, 30' is closed, e.g., adjacent to light body 20, 20' and to an opening in the housing 22, 22' thereof. Cover 32, 32' has on a surface facing the interior of light body housing 22, 22' one or more recesses for receiving one or more contact springs 36 that provide electrical contacts 36 for connecting to a source of electrical power, e.g., one of more batteries, in the cavity interior to housing 22, 22'. Cover 32, 32' is preferably an integrally molded plastic part including the hooks 32H and latch 32L, 32'L; the one or more contact springs 36 are preferably formed from a single length of spring wire. A gasket or seal 34 is preferably provided around the periphery of cover 32, 32', e.g., in a groove therein, for reducing the entry of moisture, dirt and other debris into light body 20, 20'.

Actuator 90 preferably includes a flexible circular boot that is held in place by a boot ring 46 that is attached to light head housing 42. For example, when the circular boot is pressed, it moves elements internal to light head 40 to activate, e.g., operate, an electrical switch therein which in turn selectively controls the application of electrical power to light source 80 for causing light source 80 to produce light.

An optional clip 60 may be provided on light body 20, 20' so that light 10, 10' may be attached to a person, equipment, an object, a helmet mounting device, and the like. Clip 60 is preferably of a strong springy material such as a steel, spring steel, beryllium copper, a strongly resilient plastic, and the like. Clip 60 has an elongated member 62 that extends along a side of light body 20, 20' and is sprung so as to bear at its distal end to bear against light body 20, 20', but may be moved away from body 20, 20' so that light 10, 10' may be placed onto an object, e.g., a pocket, a belt, or other object.

While clip 60 may be attached to light 10, 10' by a screw or other fastener, a preferred example clip 60 has a U-shaped or C-shaped grasping member 64 that is of a size and shape to tightly grip light body 20, 20' between the fingers thereof, thereby being quickly and easily attachable and removable from light 10, 10'. Clip 60 preferably has a keyhole shaped opening in elongated member 62 for releasably attaching light 10, 10' with clip 60 onto a compatibly sized post or button, e.g., on a helmet mount or belt mount, and for being and rotatable thereon.

The perspective views of the example portable light 10 having a movable head 40 of FIGS. 11 and 12 illustrate alternative positions of the movable head 40 thereof, and movable head 40 of light 10' is the likewise movable relative to light body 20'. In one illustration head 40 is rotated on pivoting joint 50 in a first direction relative to light body 20, 20', and in the other illustration head 40 is rotated on pivoting joint 50 in a second direction opposite to the first direction relative to light body 20, 20'. Rotating joint 50 has sufficient friction as to retain light head 40 in any desired rotational position over a rotation range of, e.g., at least ±90° and a total rotation of at least 180° relative to light body 20, 20'. Friction arises where the outer surface of hollow cylindrical member 22M and the inner surface of cylindrical bore 42S are in contact with each other. In addition, seal 50S may be of a size and material selected to increase or decrease the friction tending to retain light head 40 in a desired position.

Figure 14:
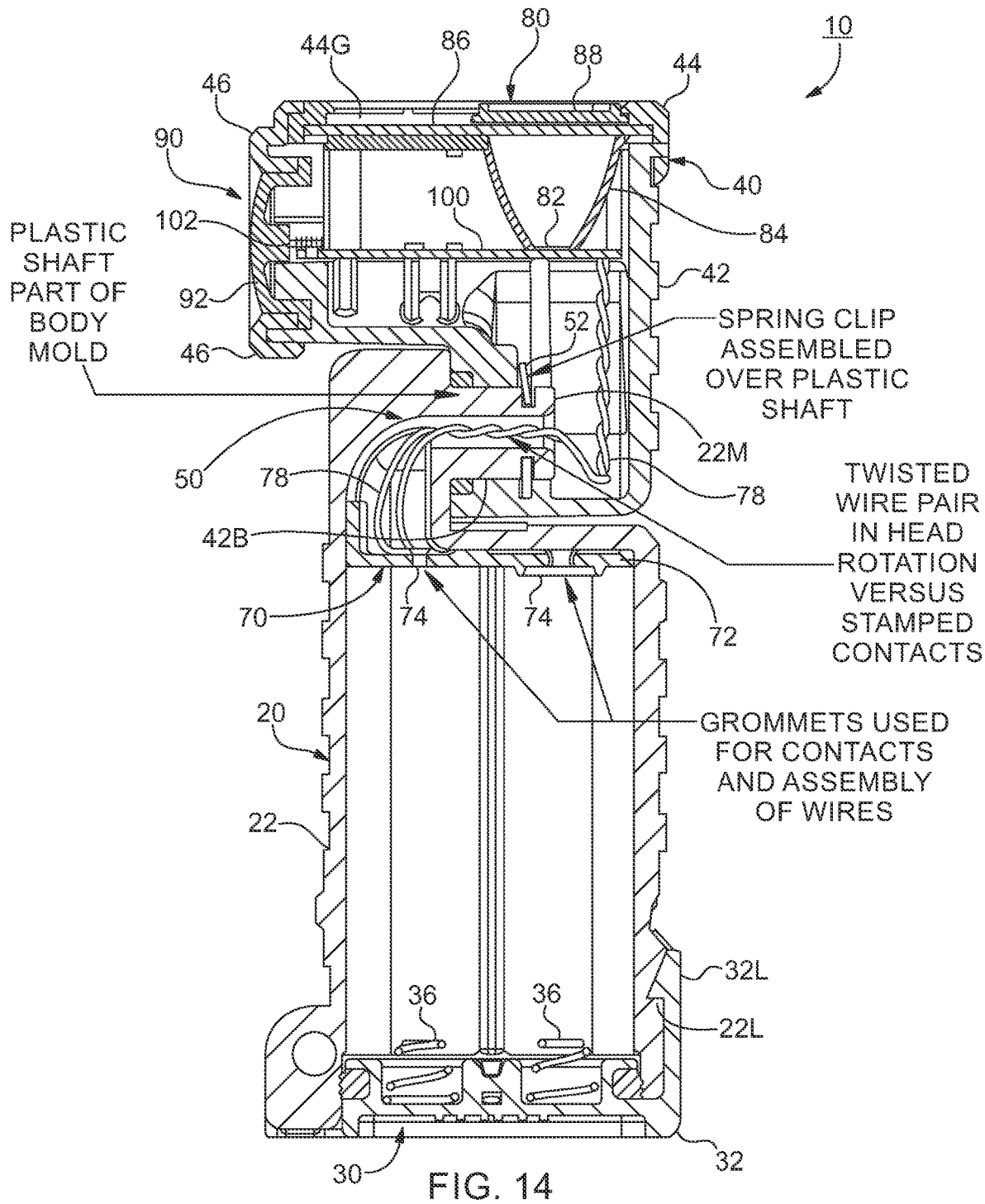
FIG. 14 is a sectional view of the example light wherein internal features thereof are visible, FIG. 14A includes inner and side views of the cover of the example light.
Figure 14A:
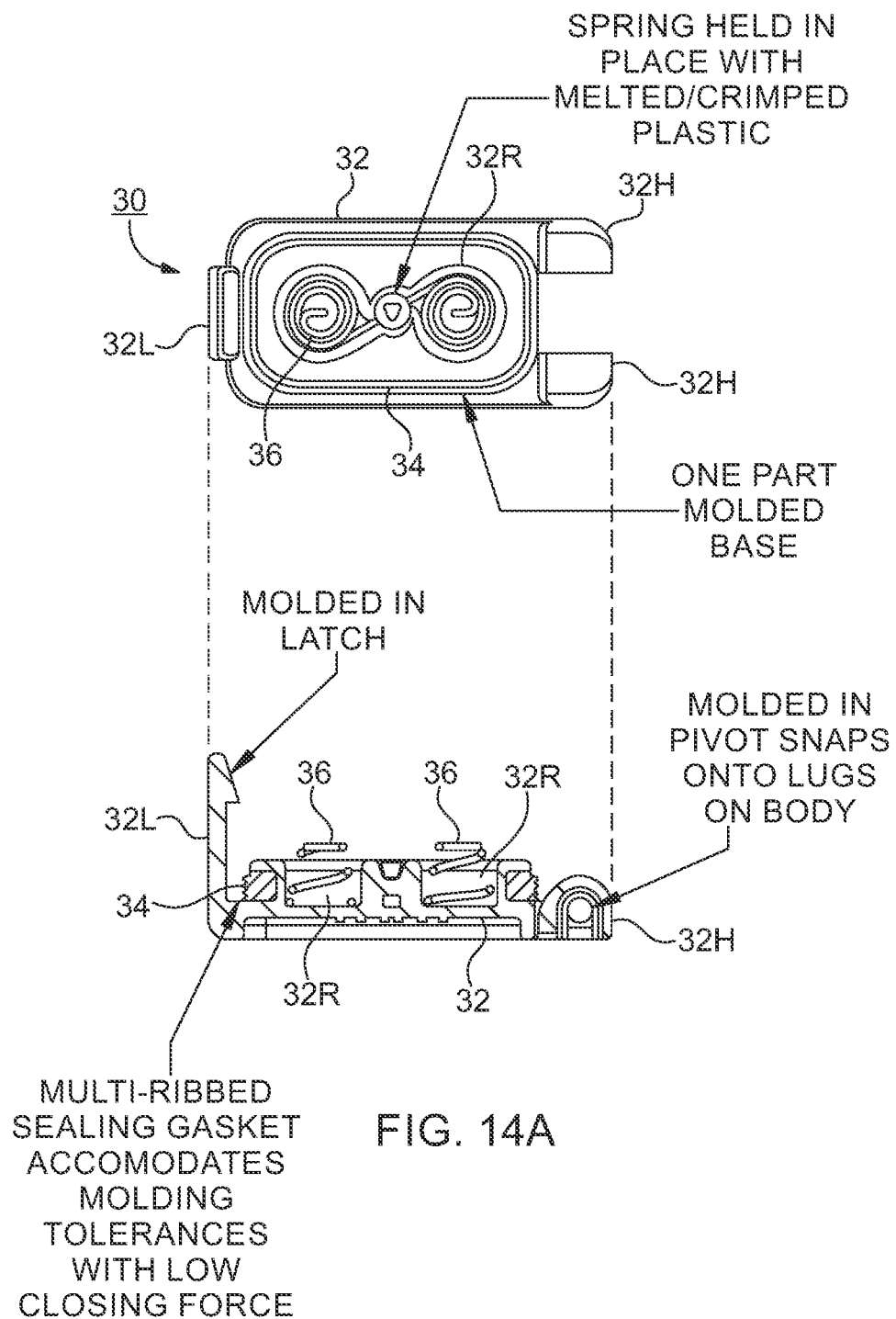
FIGS. 14B and 14C are perspective and cross-sectional views of details of the example cover and of the hinge thereof.
FIG. 14D is a sectional view of the example light wherein internal features thereof are visible.
Figure 14D:
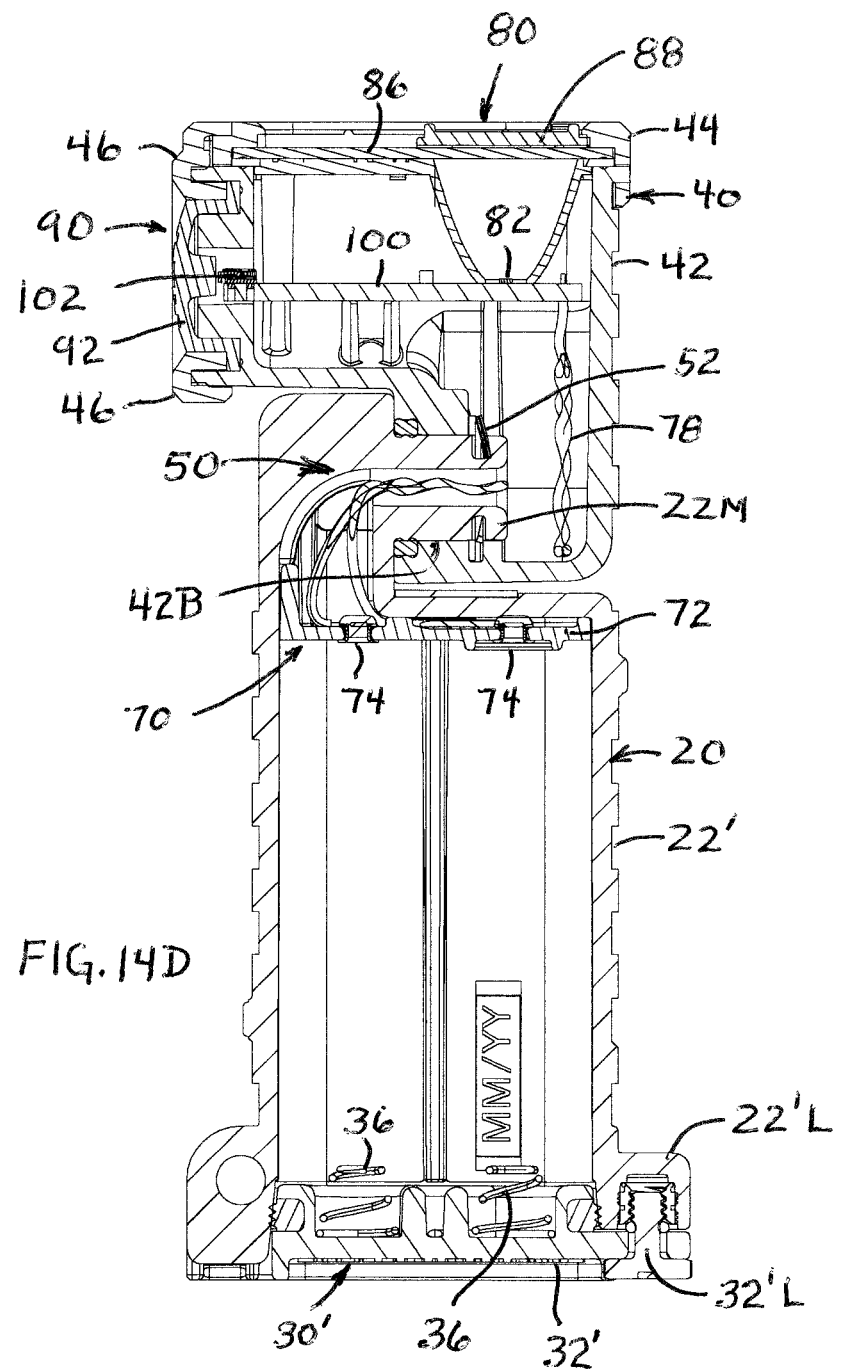
Figure 15:
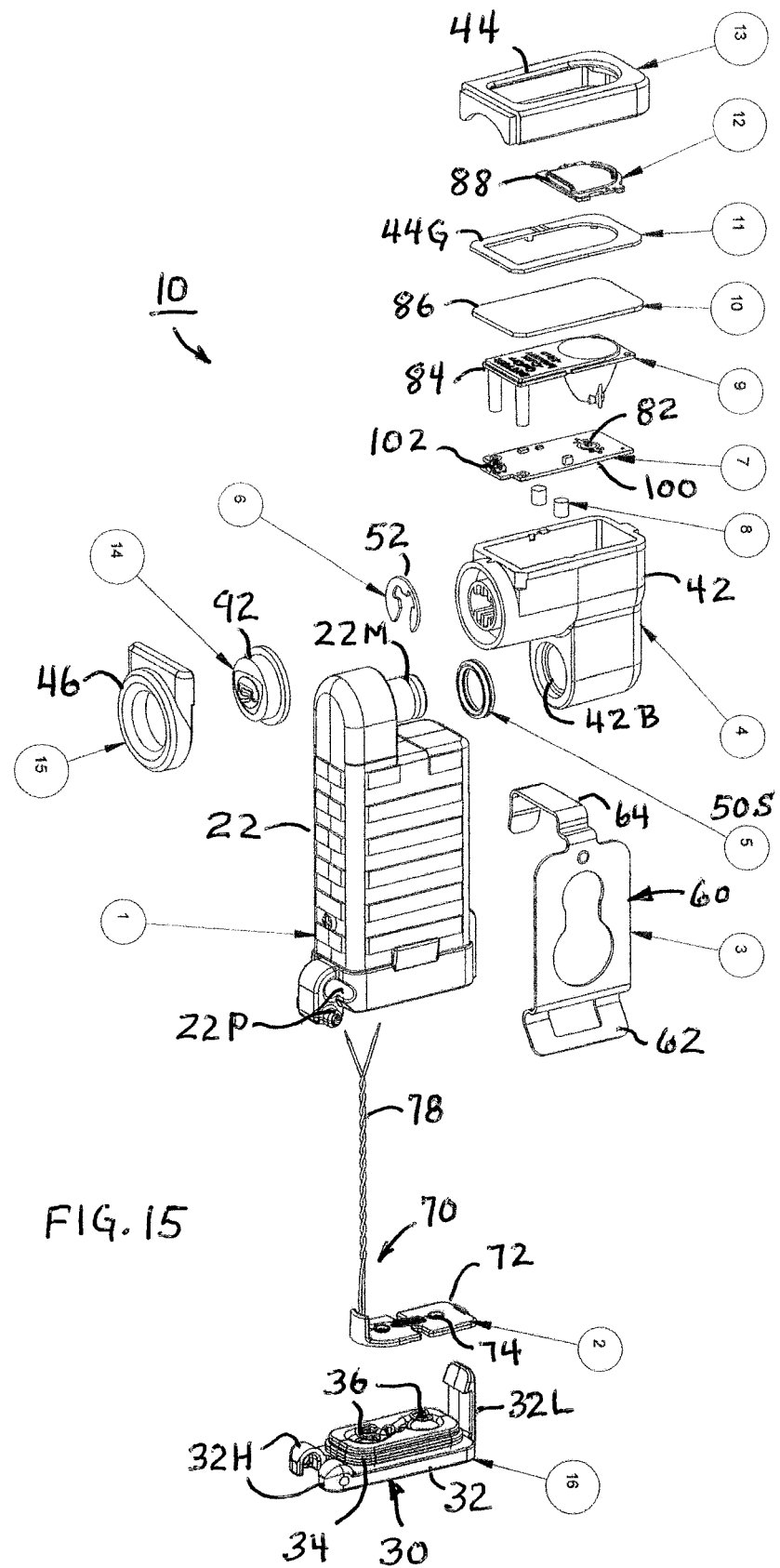
FIG. 15 is an exploded view of the example light and FIG. 15A is an exploded view of the example cover therefor.
Figure 15A:
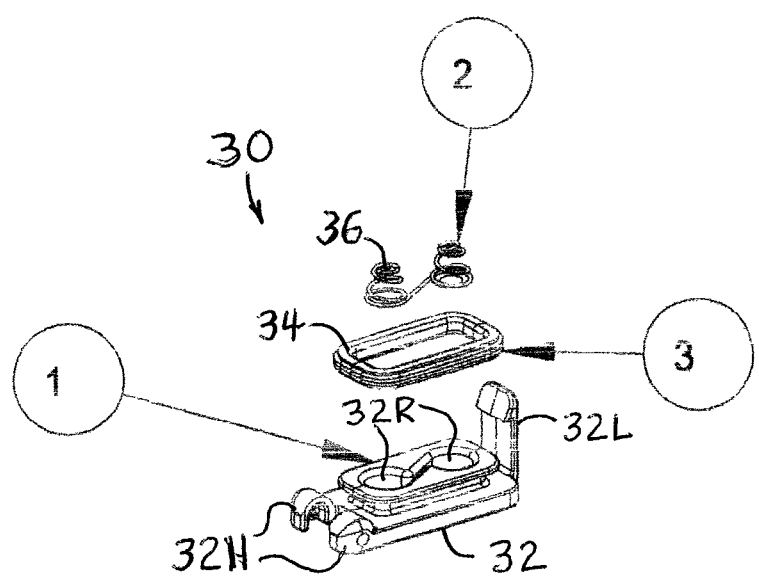
Figure 16:
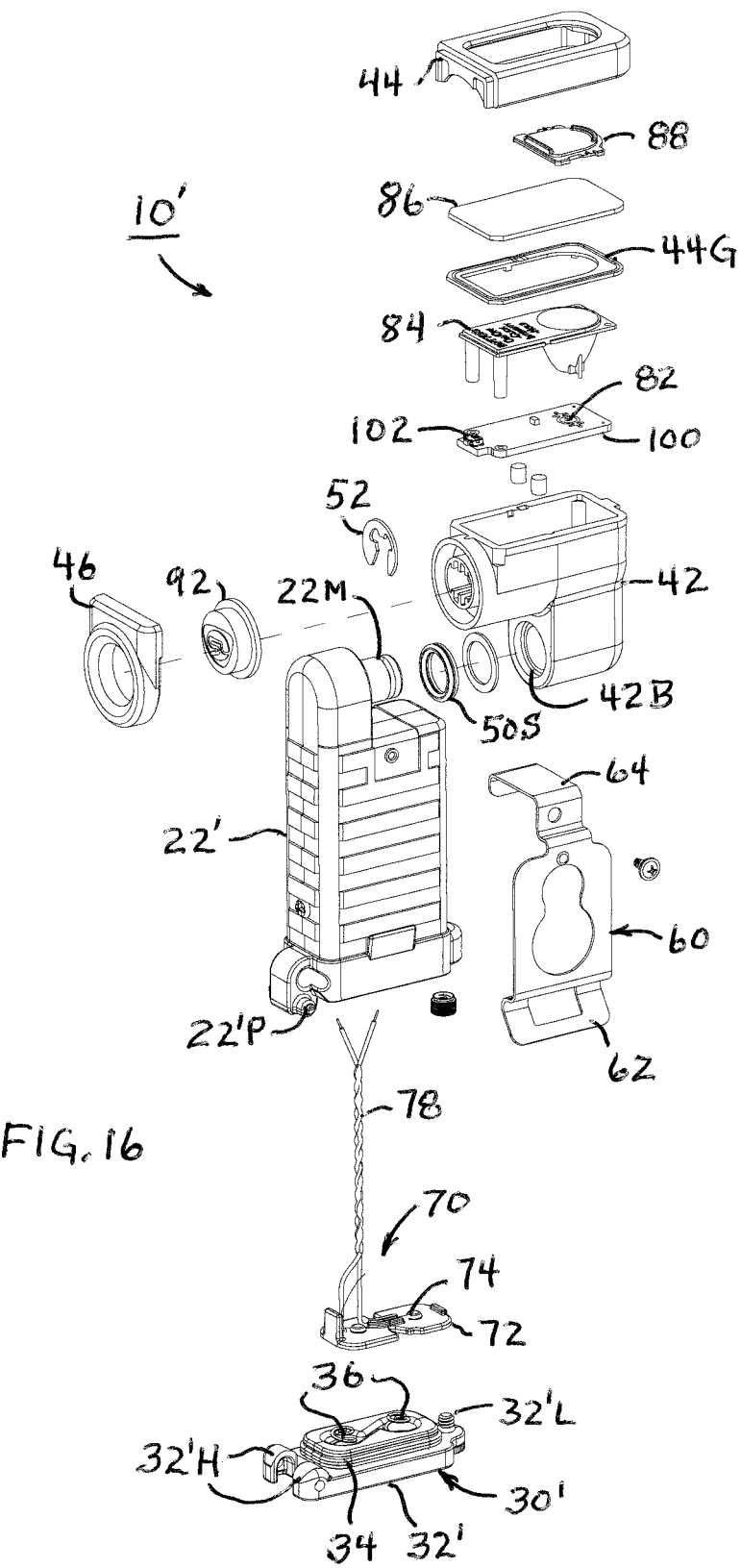
FIG. 16 is an exploded view of the other example light and FIGS. 16A and 16B are plan and side cross-sectional views, respectively, of the example cover therefor.
Figure 16A:
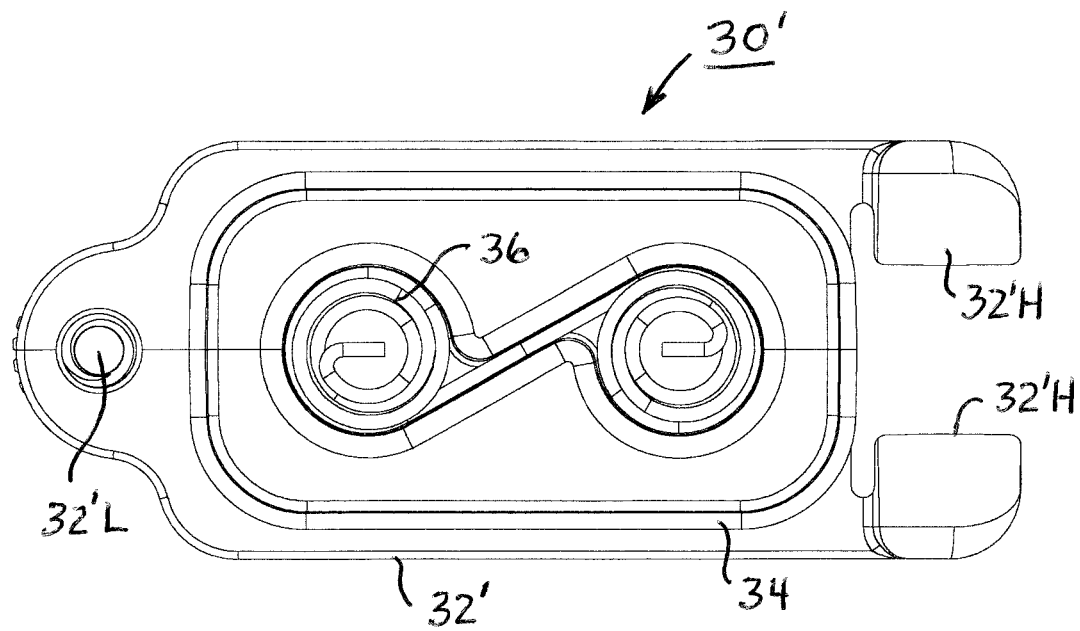
Figure 16B:
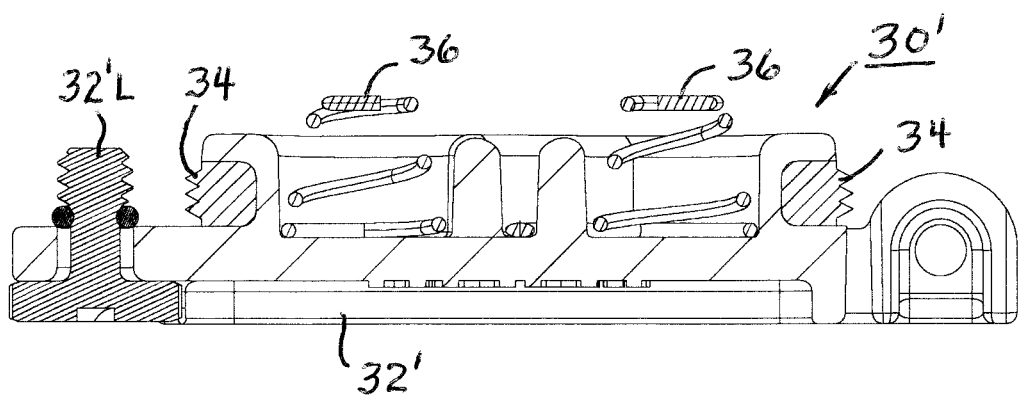

FIG. 14 is a sectional view of the example light 10 wherein internal features thereof are visible, FIG. 14A includes inner and side views of the cover 30 of the example light 10, FIGS. 14B and 14C are perspective and cross-sectional views of details of the example cover and of the hinge thereof, and FIG. 14D is a sectional view of the example light 10' wherein internal features thereof are visible; and FIG. 15 is an exploded view of the example light 10 and FIG. 15A is an exploded view of the example cover 30 therefor; FIG. 16 is an exploded view of the other example light 10' and FIGS. 16A and 16B are plan and side cross-sectional views, respectively, of the example cover 30' therefor. Light housing 20, 20' includes light body housing 22, 22' which has a cavity for receiving a source of electrical power and also includes a structure for providing one side of pivoting joint 50. Light head 40 includes light head housing 42 which has a cavity for receiving light source 80 and also include a structure for providing the other side of pivoting joint 50.

Pivoting joint 50 is provided by a pivoting or rotating joint that includes a hollow cylindrical central member extending from one of light body 20, 20' and light head 40, wherein the other of light body 20, 20' and light head has a cylindrical bore therethrough that is complementary in size and shape to the hollow cylindrical central member for receiving the hollow cylindrical central member therein. The hollow cylindrical member is longer than the cylindrical bore and so the end thereof extends through the cylindrical bore. A fastener disposed interior to the other of light body 20, 20' and light head 40 engages the end of the hollow cylindrical central member thereby to retain the hollow cylindrical central member in the cylindrical bore and provide the rotating joint 50.

In the example light 10, 10' as illustrated, hollow cylindrical central member 22M extends from body housing 22, 22' and complementary cylindrical bore 42B extends through head housing 42 wherein fastener 52 grasps the end of hollow cylindrical member 22M to retain housings 22, 22' and 42 joined together by the pivoting or rotating joint 50 of light 10, 10'. Body housing 22, 22' and head housing 42 are preferably each molded plastic parts which include the hollow cylindrical central member or the complementary cylindrical bore that provide the rotating joint 50 integrally molded therewith. Example fastener 52 may be a spring clip 52 that is seated in a circumferential groove near to the end of the hollow cylindrical central member. A seal 50S may be provided to resist moisture, dirt or other debris from entering light 10.

Battery contact assembly 70 is disposed at the upper end of the battery cavity of body housing 22, 22' for providing one or more contacts for the one or more batteries therein. Contact assembly 70 has one or more electrical contacts 74 for electrically connecting to the source of electrical power and has one or more electrical conductors 78 that extend through the hollow cylindrical central member 22M to connect to the light source 80 in light head 40.

The example contact assembly 70 includes an insulating blank 72 having at least two holes therein, and a respective electrically conductive grommet 74 in each of the at least two holes. Each grommet 74 is formed to be retained in its respective hole in the insulating blank 72 and to electrically connect to one of the at least two electrical conductors 78.

Example light source 80 includes a circuit board 100 on which are mounted a light emitting source 82, e.g., a light emitting diode (LED) 82, and an electrical switch 102 which is actuated from outside of light 10, 10' via actuator arrangement 90. Circuit board 100 may include additional electronic circuitry, e.g., a DC converter for transforming electrical power from a power source, e.g., a battery, to a voltage and/or current suitable for operating light source 80 at a desired brightness and/or providing a desired run time. Circuit board 100 may also include a microprocessor, or other processor and/or controller, for controlling the operating mode of light 10 responsive to user inputs provided via switch 102, e.g., light ON, light OFF, momentarily ON, dimmer, brighter, flashing, blinking, strobing, and the like.

Example actuator 90 typically includes a flexible boot 92 that has a peripheral shape complementary to the opening in head housing 42 in which boot 42 is disposed for forming seat there around and has a thicker central region that extends inwardly toward switch 102 to serve as a plunger for actuating switch 102 when boot 92 is pressed. A boot ring 46 retains boot 92 in retained in position on light head housing 42 and is attached thereto by any suitable fastener. In one preferred light head 40, boot ring 44 is heat welded, ultrasonically welded or adhesively attached to housing 42. Boot 92 is preferably or a rubbery or resilient plastic and is shaped so that its resiliency is sufficient to return it to its non-pressed shape (e.g., its natural relaxed shape) when pressure that is applied to it, e.g., by a user actuating light 10, 10', is released. However, a spring may be provided between boot 92 and circuit board 102 to assist boot 92 to return to its non-pressed shape and position.

Light source 80 further includes an optical element 84 for directing light produced by LED 82 in a desired beam and direction, and a relatively flat transparent lens 86 covering LED 82 and optical element 84. Optical element 84 may be a curved reflector 84, e.g., a generally parabolic reflector 84 or other curved reflective element 84, or may be a solid optical element 84, e.g., a totally internally reflective (TIR) element 84. In the illustrated embodiment, optical element 84 includes relatively flat portion that is disposed adjacent to and beneath flat lens 86 which may be used as surface for instructional and other markings for a user of light 10, 10'.

Lens 86 and optical reflector 84 are retained in place in head housing 42 by a face cap or bezel 44 that fits onto head housing 42 and is fastened thereto by any suitable fastener. In one preferred light head face cap 44 is heat welded, ultrasonically welded or adhesively attached to housing 42.

Face cap 44 is annular defining an opening that is of a size suitable for passing light emitted by light source 80 and passing through lens 86, e.g., at least a circular opening complementary to the wide end of optical reflector 84.

Preferably the opening through face cap 44 is elongated and in the illustrated embodiment, has two opposing substantially parallel longer sides and two ends, with one end being straight and the other end being semicircular and of similar size to the wide end of reflector 84. Also preferably face cap 44 has opposing grooves or slots in its substantially parallel longer sides and has a sliding optical filter 88 or lens 88 whose opposing edges ride in the opposing grooves so as to be slidable along the longer dimension of face cap 44.

Optical filter or lens 88 may be moved or slid toward the circular end of the opening of face cap 44 so as to cover the wide end of circular reflector 84 and affect the light emanating therefrom, or may be moved toward the straight end of that opening so as to not affect the light emanating from light source 80. Optical filter or lens 88 may be, e.g., a color filter, a diffusing filter, a beam spreading lens or a beam narrowing lens, or have any other optical characteristic, as may be desired.

Anti-oxidation ("deoxo") or other chemically active pellets may be provided in light head 40 to reduce the potential for degradation of the circuitry therein, and venting outlets may be provided in light body 20, 20' to relieve any pressure that the batteries therein may create, e.g., by gas escaping therefrom.

Cover 30, 30' includes a cover blank 32, 32' that is preferably a one piece molded plastic part or base. Cover blank 32, 32' has one or more hooks 32H at one end thereof that hook onto one or more complementary projections 22P of body housing 22, 22' to provide a hinged attachment of cover 30, 30' to housing 22, 22'. Preferably hooks 32H have an opening that is slightly smaller than the diameter of projections 22P so that they snap onto projections 22P, whereby cover 30, 30' does not fall off of housing 22, 22'. Cover blank 32, 32' also has a molded in latch 32L, 32'L that extends toward housing 22, 22' so as to engage a latch projection 22L, 22'L thereon when cover 32, 32' is moved to be adjacent to housing 22, 22' to cover the battery access opening at the bottom end thereof.

Regarding the cover hinge provided by hooks 32H and housing projections 22P, hooks 32H and projections 22P each have a larger primary complementary feature, e.g., a projection or a recess, that together define the pin and knuckle of the hinge and each further has a smaller complementary feature, e.g., a projection or a hole, that retains the hooks 32H on the projections 22P so that cover 30, 30' is retained and does not fall off of light housing 22, 22'. On the outer ends of each of the cylindrical hinge projections 22P is a smaller coaxial secondary projection 22P2 which is sized to fit into the smaller holes 32H2 on the outside wall of the hooks 32H. These secondary projections 22P2 hold the cover 30, 30' onto the housing 22, 22' of light body 20, 20' when the cover 30, 30' is opened up fully. Without secondary projections 22P2 the cover 30, 30' would fall off housing 22, 22' when rotated 180° away from its closed position adjacent to housing 22, 22'. The projections 22P have a chamfer that facilitates getting the projections 22P2 into the holes 32H2 when pressure is applied during the installation of cover 30, 30' so as to wedge the opposing hooks 32H apart so that they can hook over projections 22P.

The example latch 32L, 32'L for lights 10, 10' are in substantially the same locations on light body 20, 20' and perform substantially the same function, e.g., that of retaining cover 30, 30' in a closed position adjacent housing 22, 22'. Latch 32L includes a latch arm 32A that extends from cover 32 towards light body housing 22 to engage a latch feature 22L thereon when cover 30 is moved to be adjacent to housing 22, thereby to retain cover 30 in that position adjacent to housing 22. Latch 32L is released by moving the distal end of latch arm 32A away from housing 22 so as to disengage latch arm 32A from latch feature 22L.

Similarly, latch 32'L includes a latch arm 32'A that extends towards light body housing 22' to engage a latch feature 22'L thereon when cover 30' is moved to be adjacent to housing 22', thereby to retain cover 30' in that position adjacent to housing 22'. Latch arm 32'A thereof is, e.g., a threaded end of a thumb screw 32S that is rotated to engage latch feature 22'L of housing 22' which is, e.g., a correspondingly threaded opening 22'L of housing 22'. Latch 32'L is released by rotating the thumb screw 32'A out of hole 22'L of housing 22' so as to disengage latch arm 32'A from latch feature 22'L.

Cover 30 also provides one or more electrical contacts 36 for connecting to terminals of a source of electrical power in housing 22, 22'. Cover blank 32, 32' preferably has one or more recesses 32R molded therein that are of a size and shape for receiving one or more spring contacts 36 therein. In the illustrated embodiment which receives two cylindrical batteries, and so two spring contacts 36 are provided. Spring contacts 36 are preferably formed of a single length of spring wire and have two conical helical springs formed so as to extend into housing 22, 22' to contact the batteries therein. Spring contacts 36 are preferably placed into the recess 32R therefor and then are fastened therein, e.g., by heating and pressing the edges of recess 32R inward over a part of spring 36 or by adhesive and the like.

In FIG. 15 the circled numbers and item numbers therein are as follows:

| CIRCLED NUMBER | ITEM NUMBER | PART NOMENCLATURE |
| --- | --- | --- |
| 1 | 22 | Body or light body housing |
| 2 | 70 | Contact assembly or contact base assembly |
| 3 | 60 | Clip |
| 4 | 42 | Head or light head housing |
| 5 | 50S | Quad seal or O-ring |
| 6 | 52 | Spring clip or fastener |
| 7 | 100 | Circuit board or LED PCB assembly |
| 8 | — | Deoxo pellets |
| 9 | 84 | Reflector panel or optical element |
| 10 | 86 | Lens |
| 11 | 44G | Lens gasket or seal |
| 12 | 88 | Filter (Red) or optical filter |
| 13 | 44 | Face cap or face cap diffuser |
| 14 | 92 | Boot or actuator boot |
| 15 | 46 | Boot ring or boot plate |
| 16 | 30 | Battery door assembly or cover assembly |

In FIG. 15A the circled numbers and item numbers therein are as follows:

| CIRCLED NUMBER | ITEM NUMBER | PART NOMENCLATURE |
| --- | --- | --- |
| 1 | 32 | Battery door or cover blank |
| 2 | 36 | Battery door spring or spring contact |
| 3 | 34 | Battery door gasket or seal |

Figure 17:
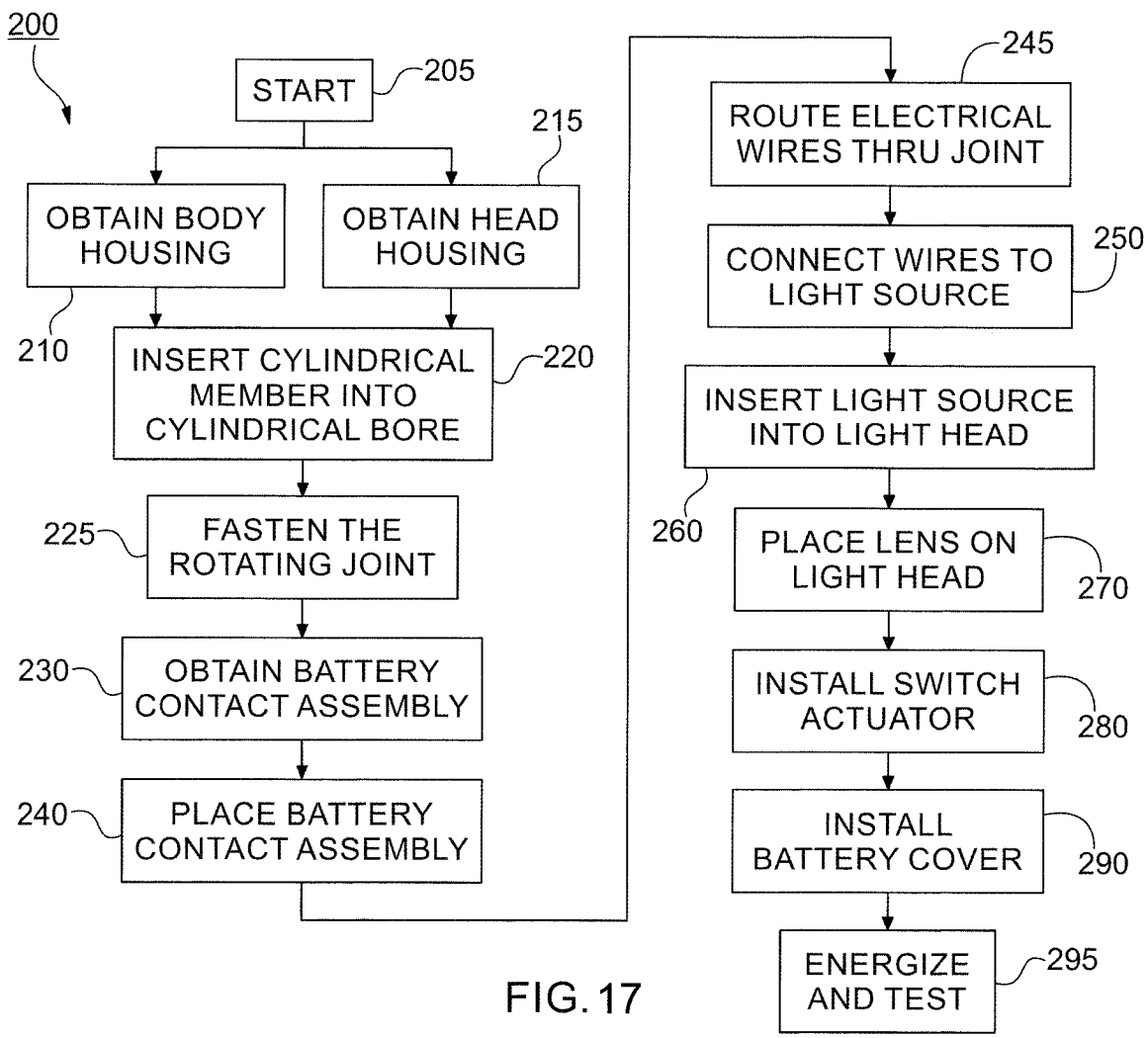
FIG. 17 is a schematic flow diagram of a method or process for assembling a portable light having a movable light head.

FIG. 17 is a schematic flow diagram of a method or process 200 for assembling a portable light 10 having a movable light head 40, and FIGS. 17A through 17E are flow diagrams illustrating various aspects 230, 250, 270, 280 of process 200. Process 200 starts 205 with the obtaining 210 a body housing 22, 22' and obtaining 215 a head housing 42, one having an extending hollow cylindrical member and the other having a complementary cylindrical bore. Inserting 220 the extending hollow cylindrical member into the cylindrical bore provides the geometry of the rotating joint 50 and fastening 225 the extending hollow cylindrical member in the cylindrical bore, e.g., by applying a fastener to the end of the hollow cylindrical member that extends through and beyond the cylindrical bore, to retain the rotating joint is an operative condition. A seal, e.g., an O-ring seal, may be positioned around the cylindrical member in the bore to provide a seal and friction.

Obtaining 230 a battery contact assembly 70 precedes placing 240 the battery contact assembly 70 into the light body housing 22, 22' and routing 245 the electrical wires (conductors) 78 thereof through the hollow interior of the hollow cylindrical member of rotating joint 50 into light head housing 42. Connecting 250 the electrical wires 78 to light source 80 is done near to head housing 80 and inserting 260 light head 80 into position in head housing 42 tends to relax the electrical wires and create slack therein. Wires 78 are soldered or otherwise electrically connected to circuit board 100.

Placing 270 lens 86 on head housing 42 over and adjacent to light source 80, retained by face cap 44, and installing 280 switch actuator 90 completes the assembly of light head 40. Installing 290 the battery cover 30, 30' on body housing 22, 22', e.g., by placing the hooks 32H thereof onto the projections 22P of body housing 22, 22', completes the assembly of portable light 10, 10' including its movable head.

Energizing 295 and testing 295 of the completed light 10, 10' may follow for some or all or none of the lights 10, 10' assembled by method 200. If energized, energizing 295 may be by connecting light 10, 10' to a suitable source of electrical power or by simply placing one or more proper batteries into the battery cavity of light body 20, 20' and closing battery cover 30, 30'.

It is noted that the steps in example method 200, as well as those in example process aspects 230-280 described below, need not be exactly followed and may be reordered as may be convenient or convenient to particular embodiments of a light 10, 10' and to assembly personnel and facilities.

Figure 17A:
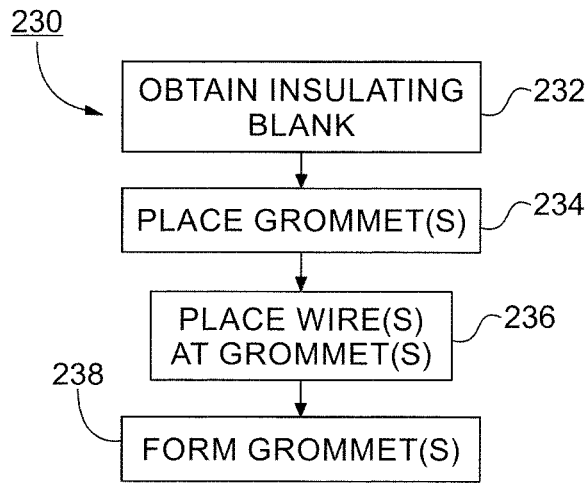

FIG. 17A is a flow diagram illustrating the aspect 230 of process 200 relating to the obtaining 230 a battery contact assembly 70. Obtaining a battery contact assembly 70 starts with obtaining 232 an insulating blank 72 having one or more holes therein, placing 234 one or more grommets 74 in the one or more holes, placing electrical conductors (wires) 78 proximate the grommet(s) and forming 238 the grommet(s) to secure the wire(s) to the grommet(s) and the grommet(s) to the insulating blank, thereby making the battery contact assembly 70.

Figure 17B:
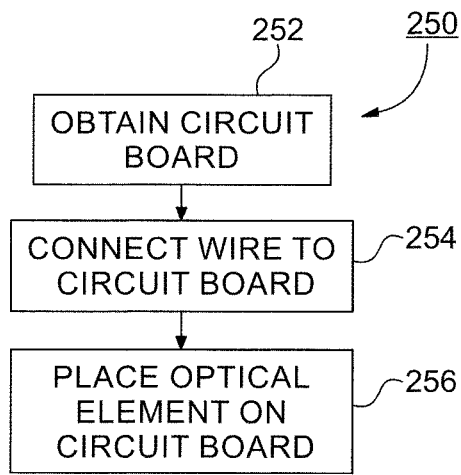

FIG. 17B is a flow diagram illustrating the aspect 250 of process 200 relating to connecting 250 the electrical wires to the light source 80. Free ends of electrical wires 78 extend through rotating joint 50 into head housing 42 and, after obtaining 252 an electronic circuit board 100, connecting 254 the ends of wires 78 to circuit board 100, e.g., by soldering, crimping or forming another suitable connection. Optical element 84, e.g., a curved reflector 84 or TIR element 84, placing 256 the optical element 84 in proper position relative to circuit board 100, e.g., before it is installed in head housing 42.

FIG. 17C is a flow diagram illustrating the aspect 270 of process 200 relating to placing 270 the lens 86 on the light head housing 42. Positioning 272 lens 86 adjacent the light source and opening of head housing 42 may precede 272 placing 274 optical filter 86 in the grooves of face cap 44 or may follow step 274 by placing 272A on face cap 44 adjacent to optical filter 88 which has already been placed therein. Placing 276 face cap 44 onto head housing 42 captures both lens 86 and optical filter 88 therebetween and then fastening 278 face cap 44 to head housing 42, e.g., by a heat welding, chemical welding, ultrasonic welding and/or adhesively attaching.

FIG. 17D is a flow diagram illustrating the aspect 280 of process 200 relating to installing 280 the switch actuator boot 92. Installing 280 switch actuator 90 includes placing 282 switch boot 92 in an opening therefor in head housing 44 and either prior thereto or thereafter, placing 284 electrical switch 102, e.g., on circuit board 100, in head housing 44. Placing 286 boot ring 46 in position on head housing 44 precedes fastening 288 boot ring 46 to head housing 44 to retain boot ring 46 and boot 96 thereon, e.g., by heat or chemical welding or using an adhesive.

FIG. 17E is a flow diagram illustrating the aspect 290 of process 200 relating to installing the battery cover 30, 30' onto light housing 22, 22'. Installing 290 battery cover 30, 30' includes obtaining 292 the cover blank 32, 32', placing 294 the sealing ring 34 into the peripheral groove therefor of cover blank 32, 32', placing 296 the spring contact 36 into the recess 32R therefor of cover blank 32, 32', and fastening 297 spring 36 therein, e.g., by heat forming or heat staking one or more edges of the recess 32R or using an adhesive, thereby completing the assembly of cover 30, 30'. Cover 30, 30' is then attached 298 to housing 22, 22' by snapping the hooks 32H thereof onto projections 22P of housing 22, 22' and closing cover 30, 30' and engage the respective latch features 32L and 22L of cover 30, 30' and housing 22, 22', respectively, either with or without placing a source of electrical power, e.g., batteries, into housing 22, 22'.

In a typical embodiment, light body 20, 20', light body housing 22, 22', cover 30, 30' cover blank 32, 32', light head 40, light head housing 42, face cap 44 and boot ring 46 are preferably made of molded plastic, each preferably as a single molded piece including the relevant features thereof, such as a molded plastic such as a nylon, engineered nylon, Nylon 6, polycarbonate, polyethylene, a PC/PET plastic blend, ABS plastic, polypropylene, polycarbonate, polyester-polycarbonate blends and ABS polycarbonate blends (such as LEXAN® polycarbonate, XENOY polyester-polycarbonate blend and CYCALOY ABS polycarbonate blend), or may be a thermoplastic nylon or other elastomeric plastic such as that sold under the trademarks CAPRON® and NYPEL® or a thermoplastic elastomer compound or thermoplastic vulcanizate sold under the trademark NYLABOND®, or any other suitable plastic or other moldable material, with or without a reinforcing material such as a fiberglass, carbon fiber or the like, and with or without a thermally conductive filler material.

Electrical conductors 78 and grommets 74 are preferably metal, e.g., copper, brass, bronze, phosphor bronze, beryllium copper, aluminum, steel, spring steel, stainless steel, or another suitable electrically conductive material.

Lens 86, optical filter 88, reflector 84 and/or TIR optical element 84 may be made of glass, polycarbonate, nylon, acrylic, PMMA, or another suitable clear, transparent or translucent plastic or other suitable material.

Clip 60 and contact spring 36 are preferably made of steel, spring steel, stainless steel, beryllium copper, or another suitable material having a spring-like character.

The foregoing materials are commercially available from many distributors and suppliers.

A portable light 10 having a movable light head 40 may comprise: a light body 20 for supporting a source of electrical power; a light head 40 for supporting a light source that produces light when energized by the source of electrical power; a rotating joint 50 joining the light body 20 and the light head 40 in movable relationship, the rotating joint 50 including: a hollow cylindrical central member extending from one of the light body 20 and the light head 40, wherein the other of the light body 20 and the light head 40 has a cylindrical bore complementary in size and shape to the hollow cylindrical central member for receiving the hollow cylindrical central member therein; and a fastener 52 disposed interior to the other of the light body 20 and the light head 40 engaging the hollow cylindrical central member of the one of the light body 20 and the light head 40 to retain the hollow cylindrical central member in the cylindrical bore of the other of the light body 20 and the light head 40; and one or more electrical conductors 78 that extend through the hollow cylindrical central member of the rotating joint 50 to connect the source of electrical power in the light body 20 to the light source in the light head 40; and an electrical switch 102 coupled in circuit with the light source and the source of electrical power via the one or more electrical conductors 78 for selectively energizing the light source to produce light. The portable light 10 having a movable light head 40 may further comprise a contact assembly disposed in the light body 20 and having one or more electrical contacts for electrically connecting to the source of electrical power. The contact assembly 70 may include an insulating blank having at least two holes therein, and a respective electrically conductive grommet in each of the at least two holes, each grommet being formed to be retained in the respective hole in the insulating blank and to electrically connect to one of the at least two electrical conductors 78. The light source 80 may include an electronic circuit board, wherein: the electronic circuit board supports the switch; or the electronic circuit board connects to the at least two electrical conductors 78; or the electronic circuit board supports the switch and connects to the at least two electrical conductors 78. The light head 40 may include a flexible actuator and wherein the electronic circuit board is positioned in the light head 40 with the switch adjacent to the flexible actuator, whereby pressing the flexible actuator actuates the switch. The light body 20 may have an opening for inserting and removing the source of electrical power and has at least one projection proximate the opening therein, the light body 20 may further comprise: a cover 30 of a size and shape for covering the opening therein, the cover 30 having: at least one hook member for engaging the at least one projection of the light body 20 thereby defining a hinge for the cover 30; or a latch for engaging the light body 20 for retaining the cover 30 against the light body 20 and covering the opening therein; or at least one hook member for engaging the at least one projection of the light body 20 thereby defining a hinge for the cover 30 and a latch for engaging the light body 20 for retaining the cover 30 against the light body and covering the opening therein. The at least one hook member has flexibility sufficient to snap onto the at least one projection of the light body 20 and to be retained thereon without a fastener. The latch may include: a latch arm extending towards the light body 20 for engaging a complementary latch member of the light body 20 for retaining the cover 30 against the light body 20 and covering the opening therein; or a fastener disposed in a hole through the cover 30 and having an engaging member extending towards the light body 20 for engaging a complementary latch member of the light body 20 for retaining the cover 30 against the light body 20 and covering the opening therein. The latch may include: a latch arm extending towards the light body 20 and having a projection for engaging a complementary latch projection of the light body 20 for retaining the cover 30 against the light body 20 and covering the opening therein; or a threaded fastener disposed in a hole through the cover 30 and having a threaded shaft extending towards the light body 20 for engaging a complementary threaded hole in the light body 20 for retaining the cover 30 against the light body 20 and covering the opening therein. The portable light 10 may further comprise a clip 60 having a U-shaped grip of a size and shape for gripping the light body 20 and an elongated member that is disposed adjacent to and along the light body 20 when the U-shaped grip is gripping the light body 20. The portable light 10 having a movable light head 40 wherein: the light source 80 of the light head 40 may include an illumination light source; or a slidable lens 88 is movable to cover and uncover the light source; or a slidable lens 88 is movable transversely on a face of the light head 40 to cover and uncover the light source; the light source 80 of the light head 40 may include an illumination light source and a slidable lens that is movable to cover and uncover the illumination light source. The slidable lens 88 may include a light filter, a colored light filter, a light diffusing filter or a combination thereof. The fastener 52 may include a threaded fastener, a bolt, a screw, a driven fastener, a pin, a rivet, a nail, a spike, a barbed fastener, a clip, a clamp, a nut, a speed nut, a cap nut, a acorn nut, a formed head, a peened head, a heat formed head, a weld, a heat weld, an ultrasonic weld, a chemical weld, a braze, an adhesive, or a combination thereof.

A portable light 10 may comprise: a light body 20 for supporting a source of electrical power; a light head 40 for supporting a light source that produces light when energized by the source of electrical power; a rotating joint 50 joining the light body 20 and the light head 40 in movable relationship, the rotating joint 50 defining an opening between the light body 20 and the light head 40; one or more electrical conductors 78 that extend through the opening of the rotating joint 50 to connect the source of electrical power in the light body 20 and the light source in the light head 40; wherein the light body 20 has an opening for inserting and removing the source of electrical power and has at least one projection proximate the opening therein, the light body 20 may further comprise: a cover 30 of a size and shape for covering the opening of the light body 20, the cover 30 having at least one hook member for engaging the at least one projection of the light body 20 thereby defining a hinge and having a latch projection for engaging the light body 20 for retaining the cover 30 against the light body 20 and covering the opening therein; and an electrical switch 102 coupled in circuit with the light source and the source of electrical power via the one or more electrical conductors 78 for selectively energizing the light source to produce light. The cover 30 may include at least one spring for making electrical contact with a source of electrical power interior to the light body 20. The cover 30 may include: a cover blank having the at least one hook member and the latch projection integral thereto, the cover blank having a recess therein for receiving at least one electrical contact; and at least one electrical contact disposed in the recess of the cover blank. The at least one electrical contact may include: one or more conical helical spring contacts formed of a single length of spring wire; or one or more conical helical spring contacts formed of a single length of spring wire that is retained in the recess of the cover blank by part of the cover blank that is formed thereover. The portable light 10 further including a sealing ring disposed in a peripheral groove of the cover blank for sealing the opening of the light body 20. The at least one hook member may have flexibility sufficient to snap onto the at least one projection of the light body 20 and to be retained thereon without a fastener. The latch may include: a latch arm extending towards the light body 20 for engaging a complementary latch member of the light body 20 for retaining the cover 30 against the light body 20 and covering the opening therein; or a fastener disposed in a hole through the cover 30 and having an engaging member extending towards the light body 20 for engaging a complementary latch member of the light body 20 for retaining the cover 30 against the light body and covering the opening therein. The latch may include: a latch arm extending towards the light body 20 and having a projection for engaging a complementary latch projection of the light body 20 for retaining the cover 30 against the light body 20 and covering the opening therein; or a threaded fastener disposed in a hole through the cover 30 and having a threaded shaft extending towards the light body 20 for engaging a complementary threaded hole in the light body 20 for retaining the cover 30 against the light body 20 and covering the opening therein. The at least one projection of the light body 20 may include two opposing larger primary projections each having a smaller secondary projection thereon, and wherein the at least one hook member may include two spaced apart hooks and a hole adjacent to each one of the hooks, the hinge including the two spaced apart hooks respectively engaging the two opposing larger primary projections with the respective smaller secondary projections extending into respective ones of the holes of the hook members. The rotating joint 50 may include: a hollow cylindrical central member extending from one of the light body 20 and the light head 40, wherein the other of the light body 20 and the light head 40 has a cylindrical bore complementary in size and shape to the hollow cylindrical central member for receiving the hollow cylindrical central member therein; and a fastener 52 disposed interior to the other of the light body 20 and the light head 40 engaging the hollow cylindrical central member of the one of the light body 20 and the light head 40 to retain the hollow cylindrical central member in the cylindrical bore of the other of the light body 20 and the light head 40. The fastener 52 may include a threaded fastener, a bolt, a screw, a driven fastener, a pin, a rivet, a nail, a spike, a barbed fastener, a clip, a clamp, a nut, a speed nut, a cap nut, a acorn nut, a formed head, a peened head, a heat formed head, a weld, a heat weld, an ultrasonic weld, a chemical weld, a braze, an adhesive, or a combination thereof. The portable light 10 may further comprise a clip having a U-shaped grip of a size and shape for gripping the light body 20 and an elongated member that is disposed adjacent to and along the light body 20 when the U-shaped grip is gripping the light body. The portable light 10 wherein: the light source of the light head 40 may include an illumination light source; or a slidable lens is movable to cover and uncover the light source; or a slidable lens is movable transversely on a face of the light head 40 to cover and uncover the light source; the light source of the light head 40 may include an illumination light source and a slidable lens is movable to cover and uncover the illumination light source. The slidable lens may include a light filter, a colored light filter, a light diffusing filter or a combination thereof. The portable light 10 may further comprise a contact assembly including an insulating blank having at least two holes therein, and a respective electrically conductive grommet in each of the at least two holes, each grommet being formed to be retained in the respective hole in the insulating blank and to electrically connect to one of the at least two electrical conductors 78.

A method 200 for assembling a light 10 may comprise: obtaining 210 a light body housing 22 either having a hollow cylindrical central member extending therefrom or a cylindrical bore complementary in size and shape to the hollow cylindrical central member; obtaining 215 a light head housing 42 having the other of a hollow cylindrical central member extending therefrom or a cylindrical bore complementary in size and shape to the hollow cylindrical central member; inserting 220 the hollow cylindrical central member into the cylindrical bore complementary in size and shape to the hollow cylindrical central member; fastening 225 the hollow cylindrical central member in the cylindrical bore to form a rotating joint 50 joining the light body housing 22 and the light head housing 42 in movable relationship; obtaining 230 a battery contact assembly having at least two electrical conductors 78 extending therefrom; placing 240 the battery contact assembly into the light body housing 22 and the at least two electrical conductors 78 through the hollow cylindrical central member into the light head housing 42; connecting 250 the at least two electrical conductors 78 to a light source; placing 260 the light source into the light head housing 42; and placing 270 a lens onto the light head housing 42 in front of the light source therein. The method 200 for assembling a light 10 wherein the fastening 225 the hollow cylindrical central member in the cylindrical bore to form a rotating joint 50 joining the light body housing 22 and the light head housing 42 in movable relationship may include applying a fastener 52 to an end of the hollow cylindrical central member that is accessible via the interior of the one of the light body housing 22 and light head housing 42 that has the cylindrical bore. The method 200 for assembling a light 10 wherein the fastening 225 may include applying a threaded fastener, a bolt, a screw, a driven fastener, a pin, a rivet, a nail, a spike, a barbed fastener, a clip, a clamp, a nut, a speed nut, a cap nut, a acorn nut, a formed head, a peened head, a heat formed head, a weld, a heat weld, an ultrasonic weld, a chemical weld, a braze, an adhesive, or a combination thereof. The method 200 for assembling a light 10 wherein the connecting the at least two electrical conductors 78 to a light source and the placing the light source into the light head housing 42 may include: electrically connecting the at least two electrical conductors 78 to an electronic circuit board including a light emitting semiconductor thereon; and placing the electronic circuit board into the light head housing 42 in an orientation such that light produced by the light emitting semiconductor is directed outwardly therefrom. The method 200 for assembling a light 10 wherein the light head housing 42 may include an electrical switch for selectively actuating the light source therein, the method 200 may further comprise: placing a flexible boot in an opening in the light head housing 42 adjacent to the electrical switch therein; and attaching a ring to the light head housing 42 to retain the flexible boot thereon. The method 200 for assembling a light 10 wherein the attaching a ring to the light head housing 42 to retain the flexible boot thereon may include: heat forming the ring on the light head housing 42, welding the ring to the light head housing 42, heat welding the ring to the light head housing 42, ultrasonically welding the ring to the light head housing 42, chemical welding the ring to the light head housing 42, brazing the ring to the light head housing 42, applying an adhesive between the ring and the light head housing 42, or a combination thereof. The method 200 for assembling a light 10 further including attaching a face cap to the light head housing 42 to retain the light source and the lens thereto. The method 200 for assembling a light 10 wherein the attaching a face cap to the light head housing 42 to retain the light source therein may include: heat forming the face cap on the light head housing 42, welding the face cap to the light head housing 42, heat welding the face cap to the light head housing 42, ultrasonically welding the face cap to the light head housing 42, chemical welding the face cap to the light head housing 42, brazing the face cap to the light head housing 42, applying an adhesive between the face cap and the light head housing 42, or a combination thereof. The method 200 for assembling a light 10 wherein the light body housing 22 has an opening therein and has at least one projection adjacent to the opening, the method 200 may further comprise: obtaining a cover 30 of complementary size and shape to the opening of the light body housing 22 and having at least one hook of a size and shape for engaging the at least one projection thereof engaging the at least one hook of the cover 30 with the at least one projection of the light body housing 22, whereby the cover 30 is hinged to the light body housing 22; and closing the cover 30 over the opening of the light body housing 22. The method 200 for assembling a light 10 wherein the cover 30 obtained may include a latch projection extending therefrom, and wherein the closing the cover 30 over the opening of the light body housing 22 may include engaging the latch projection of the cover 30 with a latch feature of the light body housing 22. The method 200 for assembling a light 10 wherein the obtaining a cover 30 may include: obtaining a cover blank having at least one hole therethrough; placing an electrically conductive grommet in the at least one hole; and forming the grommet to be retained in the at least one hole, whereby the formed grommet provides at least one electrical contact for a source of electrical power interior to the light body housing 22. The method 200 for assembling a light 10 wherein the obtaining a cover 30 may include: obtaining a cover blank having at least one recess therein for receiving a spring contact; placing an electrically conductive spring in the at least one recess; and forming one or more edges adjacent to the at least one recess to retain the electrically conductive spring in the at least one recess, whereby the electrically conductive spring provides at least one electrical spring contact for a source of electrical power interior to the light body housing 22. The method 200 for assembling a light 10 wherein the obtaining a battery contact assembly may include: obtaining a non-conductive blank having at least two holes therethrough; placing an electrically conductive grommet in each of the at least two holes; placing one of the at least two electrical conductors 78 adjacent to a respective one of the at least two grommets; and forming the at least two grommets to electrically connect each formed grommet to the respective one of the at least two electrical conductors 78 and to retain each formed grommet in the respective one of the at least two holes, whereby the formed grommets provide at least two electrical contacts for connecting to a source of electrical power interior to the light body housing 22. The method 200 for assembling a light 10 may further comprise: obtaining a face cap having grooves in opposing sides of an opening therethrough, wherein the placing a lens onto the light head housing 42 in front of the light source therein may include: placing an optical filter in the grooves of the face cap, whereby the optical filter is slidable in the grooves; placing the lens into the face cap adjacent to the optical filter; and placing the face cap on the light head housing 42 with the lens adjacent the light source therein and with the optical filter exterior to the lens on the light head.

As used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Although terms such as "front," "back," "rear," "side," "end," "top," "bottom," "up," "down," "left," "right," "upward," "downward," "forward," "backward," "under" and/or "over," "vertical," "horizontal," and the like may be used herein as a convenience in describing one or more embodiments and/or uses of the present arrangement, the articles described may be positioned in any desired orientation and/or may be utilized in any desired position and/or orientation. Such terms of position and/or orientation should be understood as being for convenience only, and not as limiting of the invention as claimed.

As used herein, the term "and/or" encompasses both the conjunctive and the disjunctive cases, so that a phrase in the form "A and/or B" encompasses "A" or "B" or "A and B." In addition, the term "at least one of" one or more elements is intended to include one of any one of the elements, more than one of any of the elements, and two or more of the elements up to and including all of the elements, and so, e.g., the phrase in the form "at least one of A, B and C" includes "A," "B," "C," "A and B," "A and C," "B and C," and "A and B and C."

A fastener as used herein may include any fastener or other fastening device that may be suitable for the described use, including threaded fasteners, e.g., bolts, screws and driven fasteners, as well as pins, rivets, nails, spikes, barbed fasteners, clips, clamps, nuts, speed nuts, cap nuts, acorn nuts, and the like. Where it is apparent that a fastener would be removable in the usual use of the example embodiment described herein, then removable fasteners would be preferred in such instances. A fastener may also include, where appropriate, other forms of fastening such as a formed head, e.g., a peened or heat formed head, a weld, e.g., a heat weld, chemical weld or ultrasonic weld, a braze, and adhesive, and the like.

While various operations, steps and/or elements of a process or method or operation may be described in an order or sequence, the operations, steps and/or elements do not need to be performed in that order or sequence, or in any particular order or sequence, unless expressly stated to require a particular order or sequence.

As used herein, the terms "connected" and "coupled" as well as variations thereof may or may not be intended to be exact synonyms, but may also encompass some similar things and some different things. The term "connected" as indicated by its context may be used generally to refer to elements that have a direct electrical and/or physical contact to each other, whereas the term "coupled" as indicated by its context may be used generally to refer to elements that have an indirect electrical and/or physical contact with each other, e.g., via one or more intermediate elements, so as to cooperate and/or interact with each other, and may include elements in direct contact as well.

The term battery is used herein to refer to an electrochemical device comprising one or more electro-chemical cells and/or fuel cells, and so a battery may include a single cell or plural cells, whether as individual units or as a packaged unit. A battery is one example of a type of an electrical power source suitable for a portable or other device. Such devices could include power sources including, but not limited to, fuel cells, super capacitors, solar cells, and the like. Any of the foregoing may be intended for a single use or for being rechargeable or for both.

Various embodiments of a battery may have one or more battery cells, e.g., one, two, three, four, or five or more battery cells, as may be deemed suitable for any particular device. A battery may employ various types and kinds of battery chemistry types, e.g., a carbon-zinc, alkaline, lead acid, nickel-cadmium (Ni—Cd), nickel-metal-hydride (NiMH) or lithium-ion (Li-Ion) battery type, of a suitable number of cells and cell capacity for providing a desired operating time and/or lifetime for a particular device, and may be intended for a single use or for being rechargeable or for both. An example herein uses two cylindrical battery cell packages, typically carbon-zinc, alkaline, Ni—Cd, NiMH, or Li-Ion battery, typically producing about 2.5-3.5 volts. It is noted that the voltages produced thereby will be higher when approaching full charge and will be lower in discharge, particularly when providing higher current and when reaching a low level of charge, e.g., becoming discharged.

The term DC converter is used herein to refer to any electronic circuit that receives at an input electrical power at one voltage and current level and provides at an output DC electrical power at a different voltage and/or current level. Examples may include a DC-DC converter, an AC-DC converter, a boost converter, a buck converter, a buck-boost converter, a single-ended primary-inductor converter (SEPIC), a series regulating element, a current level regulator, and the like. The input and output thereof may be DC coupled and/or AC coupled, e.g., as by a transformer and/or capacitor. A DC converter may or may not include circuitry for regulating a voltage and/or a current level, e.g., at an output thereof, and may have one or more outputs providing electrical power at different voltage and/or current levels and/or in different forms, e.g., AC or DC.

Further, what is stated as being "optimum" or "deemed optimum" may or may not be a true optimum condition, but is the condition deemed to be desirable or acceptably "optimum" by virtue of its being selected in accordance with the decision rules and/or criteria defined by the designer and/or applicable controlling function, e.g., the brightness and/or runtime of a given combination of power source, e.g., battery, and LED or other light source.

While the present invention has been described in terms of the foregoing example embodiments, variations within the scope and spirit of the present invention as defined by the claims following will be apparent to those skilled in the art. For example, while a single LED source is illustrated, plural LEDs and/or plural light sources, including colored light sources, infrared light sources and/or laser light sources may be employed, individually or in any desired combination.

The illustrated arrangement is intended to receive two cylindrical batteries in the cavity of light body 20, e.g., two AA or two AAA batteries, however, a single battery or more than two batteries may be employed, and the shape thereof may be cylindrical, rectangular or any other shape.

While a single slidable optical filter 88 is illustrated in relation to light head 40, and a red colored optical filter is presently thought to be desirable, more than one optical filter and/or lens may be provided, and any optical filter 88 that is provided may be selected to affect any particular optical characteristic of the light being emitted, e.g., color, diffusion, beam shape, beam intensity uniformity, and the like.

While certain features may be described as a raised feature, e.g., a ridge, boss, flange, projection or other raised feature, such feature may be positively formed or may be what remains after a recessed feature, e.g., a groove, slot, hole, indentation, recess or other recessed feature, is made. Similarly, while certain features may be described as a recessed feature, e.g., a groove, slot, hole, indentation, recess or other recessed feature, such feature may be positively formed or may be what remains after a raised feature, e.g., a ridge, boss, flange, projection or other raised feature, is made.

Each of the U.S. Provisional Applications, U.S. Patent Applications, and/or U.S. Patents, identified herein is hereby incorporated herein by reference in its entirety, for any purpose and for all purposes irrespective of how it may be referred to or described herein.

Finally, numerical values stated are typical or example values, are not limiting values, and do not preclude substantially larger and/or substantially smaller values. Values in any given embodiment may be substantially larger and/or may be substantially smaller than the example or typical values stated.

What is claimed is:

1. A portable light having a movable light head comprising:
   a light body for supporting a source of electrical power;
   a light head for supporting a light source that produces light when energized by the source of electrical power;
   a rotating joint joining said light body and said light head in movable relationship, the rotating joint including:
      a hollow cylindrical central member extending from one of the light body and the light head, wherein the other of said light body and said light head has a cylindrical bore complementary in size and shape to the hollow cylindrical central member for receiving the hollow cylindrical central member therein; and
      a fastener disposed interior to the other of said light body and said light head engaging the hollow cylindrical central member of the one of said light body and said light head to retain the hollow cylindrical central member in the cylindrical bore of the other of said light body and said light head; and
   one or more electrical conductors that extend through the hollow cylindrical central member of said rotating joint to connect the source of electrical power in said light body to the light source in said light head; and
   an electrical switch coupled in circuit with the light source and the source of electrical power via the one or more electrical conductors for selectively energizing the light source to produce light.

2. The portable light having a movable light head of claim 1 further comprising a contact assembly disposed in said light body and having one or more electrical contacts for electrically connecting to the source of electrical power.

3. The portable light having a movable light head of claim 2 wherein said contact assembly includes an insulating blank having at least two holes therein, and a respective electrically conductive grommet in each of the at least two holes, each grommet being formed to be retained in the respective hole in the insulating blank and to electrically connect to one of the at least two electrical conductors.

4. The portable light having a movable light head of claim 1 wherein said light source includes an electronic circuit board, wherein:

said electronic circuit board supports said switch; or said electronic circuit board connects to the at least two electrical conductors; or said electronic circuit board supports said switch and connects to the at least two electrical conductors.

5. The portable light having a movable light head of claim 4 wherein said light head includes a flexible actuator and wherein said electronic circuit board is positioned in said light head with said switch adjacent to said flexible actuator, whereby pressing said flexible actuator actuates said switch.

6. The portable light having a movable light head of claim 1 wherein said light body has an opening for inserting and removing the source of electrical power and has at least one projection proximate the opening therein, said light body further comprising:

a cover of a size and shape for covering the opening therein, said cover having:

at least one hook member for engaging the at least one projection of said light body thereby defining a hinge for said cover; or a latch for engaging said light body for retaining said cover against said light body and covering the opening therein; or at least one hook member for engaging the at least one projection of said light body thereby defining a hinge for said cover and a latch for engaging said light body for retaining said cover against said light body and covering the opening therein.

7. The portable light having a movable light head of claim 6 wherein the at least one hook member has flexibility sufficient to snap onto the at least one projection of said light body and to be retained thereon without a fastener.

8. The portable light having a movable light head of claim 6 wherein said latch includes:

a latch arm extending towards said light body for engaging a complementary latch member of said light body for retaining said cover against said light body and covering the opening therein; or a fastener disposed in a hole through said cover and having an engaging member extending towards said light body for engaging a complementary latch member of said light body for retaining said cover against said light body and covering the opening therein.

9. The portable light having a movable light head of claim 6 wherein said latch includes:

a latch arm extending towards said light body and having a projection for engaging a complementary latch projection of said light body for retaining said cover against said light body and covering the opening therein; or a threaded fastener disposed in a hole through said cover and having a threaded shaft extending towards said light body for engaging a complementary threaded hole in said light body for retaining said cover against said light body and covering the opening therein.

10. The portable light having a movable light head of claim 1 further comprising a clip having a U-shaped grip of a size and shape for gripping said light body and an elongated member that is disposed adjacent to and along said light body when the U-shaped grip is gripping said light body.

11. The portable light having a movable light head of claim 1 wherein:

the light source of said light head includes an illumination light source; or a slidable lens is movable to cover and uncover the light source; or a slidable lens is movable transversely on a face of said light head to cover and uncover the light source;

the light source of said light head includes an illumination light source and a slidable lens is movable to cover and uncover the illumination light source.

12. The portable light having a movable light head of claim 11 wherein said slidable lens includes a light filter, a colored light filter, a light diffusing filter or a combination thereof.

13. The portable light having a movable light head of claim 1 wherein the fastener includes a threaded fastener, a bolt, a screw, a driven fastener, a pin, a rivet, a nail, a spike, a barbed fastener, a clip, a clamp, a nut, a speed nut, a cap nut, a acorn nut, a formed head, a peened head, a heat formed head, a weld, a heat weld, an ultrasonic weld, a chemical weld, a braze, an adhesive, or a combination thereof.

14. A portable light having a movable light head comprising:

a light body for supporting a source of electrical power;

a light head for supporting a light source that produces light when energized by the source of electrical power;

a rotating joint joining said light body and said light head in movable relationship, the rotating joint defining an opening between said light body and said light head;

one or more electrical conductors that extend through the opening of said rotating joint to connect the source of electrical power in said light body and the light source in said light head;

wherein said light body has an opening for inserting and removing the source of electrical power and has at least one projection proximate the opening therein, said light body further comprising:

a cover of a size and shape for covering the opening of said light body, said cover having at least one hook member for engaging the at least one projection of said light body thereby defining a hinge and having a latch for engaging said light body for retaining said cover against said light body and covering the opening therein; and an electrical switch coupled in circuit with the light source and the source of electrical power via the one or more electrical conductors for selectively energizing the light source to produce light.

15. The portable light having a movable light head of claim 14 wherein said cover includes at least one spring for making electrical contact with a source of electrical power interior to said light body.

16. The portable light having a movable light head of claim 14 wherein said cover includes:

a cover blank having the at least one hook member and a part of the latch integral thereto, said cover blank having a recess therein for receiving at least one electrical contact; and at least one electrical contact disposed in the recess of said cover blank.

17. The portable light having a movable light head of claim 16 wherein said at least one electrical contact includes:

one or more conical helical spring contacts formed of a single length of spring wire; or one or more conical helical spring contacts formed of a single length of spring wire that is retained in the recess of said cover blank by part of said cover blank that is formed thereover.

18. The portable light having a movable light head of claim 16 further including a sealing ring disposed in a peripheral groove of said cover blank for sealing the opening of said light body.

19. The portable light having a movable light head of claim 14 wherein the at least one hook member has flexibility sufficient to snap onto the at least one projection of said light body and to be retained thereon without a fastener.

20. The portable light having a movable light head of claim 14 wherein said latch includes:
   a latch arm extending towards said light body for engaging a complementary latch member of said light body for retaining said cover against said light body and covering the opening therein; or
   a fastener disposed in a hole through said cover and having an engaging member extending towards said light body for engaging a complementary latch member of said light body for retaining said cover against said light body and covering the opening therein.

21. The portable light having a movable light head of claim 14 wherein said latch includes:
   a latch arm extending towards said light body and having a projection for engaging a complementary latch projection of said light body for retaining said cover against said light body and covering the opening therein; or
   a threaded fastener disposed in a hole through said cover and having a threaded shaft extending towards said light body for engaging a complementary threaded hole in said light body for retaining said cover against said light body and covering the opening therein.

22. The portable light having a movable light head of claim 14 wherein the at least one projection of said light body includes two opposing larger primary projections each having a smaller secondary projection thereon, and wherein the at least one hook member includes two spaced apart hooks and a hole adjacent to each one of the hooks, the hinge including the two spaced apart hooks respectively engaging the two opposing larger primary projections with the respective smaller secondary projections extending into respective ones of the holes of the hook members.

23. The portable light having a movable light head of claim 14 wherein said rotating joint includes:
   a hollow cylindrical central member extending from one of the light body and the light head, wherein the other of said light body and said light head has a cylindrical bore complementary in size and shape to the hollow cylindrical central member for receiving the hollow cylindrical central member therein; and
   a fastener disposed interior to the other of said light body and said light head engaging the hollow cylindrical central member of the one of said light body and said light head to retain the hollow cylindrical central member in the cylindrical bore of the other of said light body and said light head.

24. The portable light having a movable light head of claim 23 wherein the fastener includes a threaded fastener, a bolt, a screw, a driven fastener, a pin, a rivet, a nail, a spike, a barbed fastener, a clip, a clamp, a nut, a speed nut, a cap nut, a acorn nut, a formed head, a peened head, a heat formed head, a weld, a heat weld, an ultrasonic weld, a chemical weld, a braze, an adhesive, or a combination thereof.

25. The portable light having a movable light head of claim 14 further comprising a clip having a U-shaped grip of a size and shape for gripping said light body and an elongated member that is disposed adjacent to and along said light body when the U-shaped grip is gripping said light body.

26. The portable light having a movable light head of claim 14 wherein:
   the light source of said light head includes an illumination light source; or
   a slidable lens is movable to cover and uncover the light source; or
   a slidable lens is movable transversely on a face of said light head to cover and uncover the light source;
   the light source of said light head includes an illumination light source and a slidable lens is movable to cover and uncover the illumination light source.

27. The portable light having a movable light head of claim 26 wherein said slidable lens includes a light filter, a colored light filter, a light diffusing filter or a combination thereof.

28. The portable light having a movable light head of claim 14 further comprising a contact assembly including an insulating blank having at least two holes therein, and a respective electrically conductive grommet in each of the at least two holes, each grommet being formed to be retained in the respective hole in the insulating blank and to electrically connect to one of the at least two electrical conductors.

29. A method for assembling a light having a movable light head comprising:
   obtaining a light body housing either having a hollow cylindrical central member extending therefrom or a cylindrical bore complementary in size and shape to the hollow cylindrical central member;
   obtaining a light head housing having the other of a hollow cylindrical central member extending therefrom or a cylindrical bore complementary in size and shape to the hollow cylindrical central member;
   inserting the hollow cylindrical central member into the cylindrical bore complementary in size and shape to the hollow cylindrical central member;
   fastening the hollow cylindrical central member in the cylindrical bore to form a rotating joint joining the light body housing and the light head housing in movable relationship;
   obtaining a battery contact assembly having at least two electrical conductors extending therefrom;
   placing the battery contact assembly into the light body housing and the at least two electrical conductors through the hollow cylindrical central member into the light head housing;
   connecting the at least two electrical conductors to a light source;
   placing the light source into the light head housing; and
   placing a lens onto the light head housing in front of the light source therein.

30. The method for assembling a light having a movable light head of claim 29 wherein the fastening the hollow cylindrical central member in the cylindrical bore to form a rotating joint joining the light body housing and the light head housing in movable relationship includes applying a fastener to an end of the hollow cylindrical central member that is accessible via the interior of the one of the light body housing and light head housing that has the cylindrical bore.

31. The method for assembling a light having a movable light head of claim 30 wherein the fastening includes applying a threaded fastener, a bolt, a screw, a driven fastener, a pin, a rivet, a nail, a spike, a barbed fastener, a clip, a clamp, a nut, a speed nut, a cap nut, a acorn nut, a formed head, a peened head, a heat formed head, a weld, a heat weld, an ultrasonic weld, a chemical weld, a braze, an adhesive, or a combination thereof.

32. The method for assembling a light having a movable light head of claim 29 wherein the connecting the at least two electrical conductors to a light source and the placing the light source into the light head housing include:
- electrically connecting the at least two electrical conductors to an electronic circuit board including a light emitting semiconductor thereon; and
- placing the electronic circuit board into the light head housing in an orientation such that light produced by the light emitting semiconductor is directed outwardly therefrom.

33. The method for assembling a light having a movable light head of claim 29 wherein the light head housing includes an electrical switch for selectively actuating the light source therein, the method further comprising:
- placing a flexible boot in an opening in the light head housing adjacent to the electrical switch therein; and
- attaching a ring to the light head housing to retain the flexible boot thereon.

34. The method for assembling a light having a movable light head of claim 33 wherein the attaching a ring to the light head housing to retain the flexible boot thereon includes: heat forming the ring on the light head housing, welding the ring to the light head housing, heat welding the ring to the light head housing, ultrasonically welding the ring to the light head housing, chemical welding the ring to the light head housing, brazing the ring to the light head housing, applying an adhesive between the ring and the light head housing, or a combination thereof.

35. The method for assembling a light having a movable light head of claim 29 further including attaching a face cap to the light head housing to retain the light source and the lens thereto.

36. The method for assembling a light having a movable light head of claim 35 wherein the attaching a face cap to the light head housing to retain the light source therein includes: heat forming the face cap on the light head housing, welding the face cap to the light head housing, heat welding the face cap to the light head housing, ultrasonically welding the face cap to the light head housing, chemical welding the face cap to the light head housing, brazing the face cap to the light head housing, applying an adhesive between the face cap and the light head housing, or a combination thereof.

37. The method for assembling a light having a movable light head of claim 29 wherein the light body housing has an opening therein and has at least one projection adjacent to the opening, the method further comprising:
- obtaining a cover of complementary size and shape to the opening of the light body housing and having at least one hook of a size and shape for engaging the at least one projection thereof;
- engaging the at least one hook of the cover with the at least one projection of the light body housing, whereby the cover is hinged to the light body housing; and
- closing the cover over the opening of the light body housing.

38. The method for assembling a light having a movable light head of claim 37 wherein the obtaining a cover includes obtaining a cover having a latch projection extending therefrom, and wherein the closing the cover over the opening of the light body housing includes engaging the latch projection of the cover with a latch feature of the light body housing.

39. The method for assembling a light having a movable light head of claim 37 wherein the obtaining a cover includes:
- obtaining a cover having a latch arm extending towards the light body for engaging a complementary latch member of the light body for retaining the cover against the light body and covering the opening therein; or
- obtaining a cover having a fastener disposed in a hole through the cover and having an engaging member extending towards the light body for engaging a complementary latch member of the light body for retaining the cover against the light body and covering the opening therein.

40. The method for assembling a light having a movable light head of claim 37 wherein obtaining a cover includes:
- obtaining a cover having a latch arm extending towards the light body and having a projection for engaging a complementary latch projection of the light body for retaining the cover against the light body and covering the opening therein; or
- obtaining a cover having a threaded fastener disposed in a hole through the cover and having a threaded shaft extending towards the light body for engaging a complementary threaded hole in the light body for retaining the cover against the light body and covering the opening therein.

41. The method for assembling a light having a movable light head of claim 37 wherein the obtaining a cover includes:
- obtaining a cover blank having at least one hole therethrough;
- placing an electrically conductive grommet in the at least one hole; and
- forming the grommet to be retained in the at least one hole,
- whereby the formed grommet provides at least one electrical contact for a source of electrical power interior to the light body housing.

42. The method for assembling a light having a movable light head of claim 37 wherein the obtaining a cover includes:
- obtaining a cover blank having at least one recess therein for receiving a spring contact;
- placing an electrically conductive spring in the at least one recess; and
- forming one or more edges adjacent to the at least one recess to retain the electrically conductive spring in the at least one recess,
- whereby the electrically conductive spring provides at least one electrical spring contact for a source of electrical power interior to the light body housing.

43. The method for assembling a light having a movable light head of claim 29 wherein the obtaining a battery contact assembly includes:
- obtaining a non-conductive blank having at least two holes therethrough;
- placing an electrically conductive grommet in each of the at least two holes;
- placing one of the at least two electrical conductors adjacent to a respective one of the at least two grommets; and
- forming the at least two grommets to electrically connect each formed grommet to the respective one of the at least two electrical conductors and to retain each formed grommet in the respective one of the at least two holes, whereby the formed grommets provide at least two electrical contacts for connecting to a source of electrical power interior to the light body housing.

44. The method for assembling a light having a movable light head of claim 29 further comprising:

obtaining a face cap having grooves in opposing sides of an opening therethrough, wherein the placing a lens onto the light head housing in front of the light source therein includes:

placing an optical filter in the grooves of the face cap, whereby the optical filter is slidable in the grooves;

placing the lens into the face cap adjacent to the optical filter; and placing the face cap on the light head housing with the lens adjacent the light source therein and with the optical filter exterior to the lens on the light head.

* * * * *